(12) United States Patent
Sanderson et al.

(10) Patent No.: US 8,759,360 B2
(45) Date of Patent: Jun. 24, 2014

(54) PURINE COMPOUNDS

(75) Inventors: Adam Jan Sanderson, Baskingstoke (GB); Peter Charles Astles, Surrey (GB); Rossella Guidetti, Baskingstoke (GB); Sean Patrick Hollinshead, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 476 days.

(21) Appl. No.: 13/072,843

(22) Filed: Mar. 28, 2011

(65) Prior Publication Data

US 2011/0245255 A1 Oct. 6, 2011

Related U.S. Application Data

(60) Provisional application No. 61/319,521, filed on Mar. 31, 2010.

(51) Int. Cl.
*A61K 31/52* (2006.01)
*C07D 473/32* (2006.01)

(52) U.S. Cl.
USPC ........................................ 514/263.2; 544/277

(58) Field of Classification Search
USPC ........................................ 544/277; 514/263.2
See application file for complete search history.

(56) References Cited

U.S. PATENT DOCUMENTS

| 4,728,644 A | 3/1988 | Yuki et al. |
| 5,057,517 A * | 10/1991 | Johnston et al. ......... 514/252.16 |
| 2003/0139427 A1 | 7/2003 | Castelhano et al. |

FOREIGN PATENT DOCUMENTS

| EP | 0300726 A1 | 1/1989 |
| WO | 03/22214 A2 | 3/2003 |
| WO | 2004037823 A1 | 5/2004 |
| WO | 2005/067546 A2 | 7/2005 |
| WO | 2006/128172 A2 | 11/2006 |
| WO | 2010019762 A1 | 2/2010 |
| WO | 2010/080306 | 7/2010 |

OTHER PUBLICATIONS

Wolf, Sherry. European Journal of Cancer 44 (2008) 1507-1515.*
J Guindon, et al., Cannabinoid CB2 receptors: a therapeutic target for the treatment of inflammatory and neuropathic pain, British Journal of Pharmacology, 2008, vol. 153, No. 2, pp. 319-334.
David A Griffith, et al., Discovery of 1-[9-(4-Chlorophenyl)-8-(2-chlorophenyl)-9H-purin-6-yl]-4-ethylamnino-piperidine-4-carboxylic Acid Amide Hydrochloride (CP-945,598), a Novel, Potent, and Selective Cannabinoid Type 1 Receptor Antagonist, Journal of Med. Chem., 2008, vol. 52, No. 2, pp. 234-237.

* cited by examiner

*Primary Examiner* — Golam M M Shameem
*Assistant Examiner* — Laura Daniel
(74) *Attorney, Agent, or Firm* — R. Craig Tucker

(57) ABSTRACT

A compound of the formula:

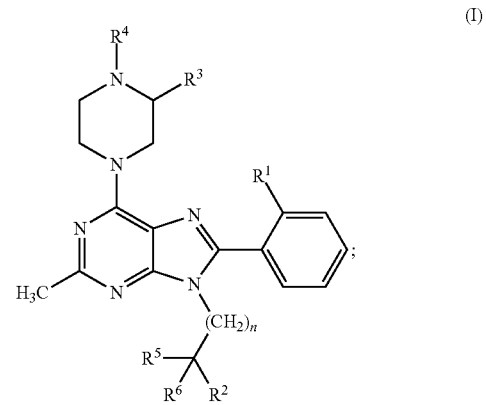

and pharmaceutical compositions for the treatment or prevention of pain.

17 Claims, No Drawings

PURINE COMPOUNDS

This U.S. application claims priority to U.S. provisional application Ser. No. 61/319,521, filed Mar. 31, 2010.

Cannabinoid receptors $CB_1$ and $CB_2$ belong to the class of G-protein-coupled receptors (GPCRs). $CB_1$ receptors are expressed both centrally and peripherally while $CB_2$ receptors are predominately expressed peripherally, primarily on immune cells and tissues.

The pharmacological and therapeutic potential of the $CB_2$ receptor has been reviewed recently (Br. J. Pharmacol. (2008) 153, 319-334) identifying $CB_2$ as a therapeutic target for the treatment of pain, in particular, inflammatory and neuropathic pain.

$CB_2$ agonists, in particular $CB_2$-selective agonists, provide a target for treating pain with limited centrally mediated side effects.

WO 2004/037823 is directed to purine compounds and use thereof as cannabinoid receptor ligands, in particular as $CB_1$ receptor antagonists.

As a consequence of side effects associated with current oral pharmacological agents, there continues to be a need for the development of alternative therapies for the treatment of pain.

The present invention provides a compound of the formula:

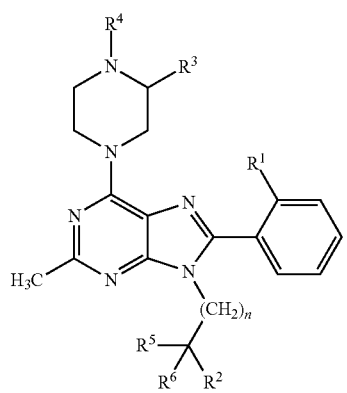

(I)

wherein;
$R^1$ is Cl or $CH_3$;
$R^2$ is OH, $OCH_3$, $CH_2OH$ or $CH_2OCH_3$;
$R^3$ is H or combines with $R^4$ to form a fused pyrrolidin-2-one;
$R^4$ is $C_1$-$C_2$ alkyl, $C_1$-$C_2$ fluoroalkyl, $C(O)CH_3$ or $CO_2CH_3$;
$R^5$ is H, $CH_3$ or $CH_2OCH_3$;
$R^6$ is H, $CH_3$ or combines with $R^5$ to form a cyclopropane ring; and
n is 0 or 1;
or a pharmaceutically acceptable salt thereof.

Compounds of the present invention have been found to be agonists of the $CB_2$ receptor in vitro. Certain compounds of the present invention exhibit greater potency than existing $CB_2$ agonists. Certain compounds of the present invention are $CB_2$-selective agonists. Certain compounds of the present invention exhibit greater $CB_2$-selectivity than existing $CB_2$ agonists. Certain compounds of the present invention exhibit potential for an acceptable side effect profile in humans.

The present invention provides a pharmaceutical composition comprising a compound of the present invention, or a pharmaceutically acceptable salt thereof, and a pharmaceutically acceptable diluent or carrier. Further, the present invention provides a pharmaceutical composition comprising a compound of the present invention, or a pharmaceutically acceptable salt thereof, together with a pharmaceutically acceptable diluent or carrier and optionally one or more other therapeutic ingredients.

The present invention provides a compound, or a pharmaceutically acceptable salt thereof, for use in therapy. The present invention also provides a compound, or a pharmaceutically acceptable salt thereof for use in the treatment of pain, in particular osteoarthritic pain. In another aspect of the present invention, there is provided the use of a compound, or a pharmaceutically acceptable salt thereof, for the manufacture of a medicament for the treatment of pain, in particular osteoarthritic pain.

In another aspect of the present invention, there is provided the use of a compound, or a pharmaceutically acceptable salt thereof, for the manufacture of a medicament for the treatment or prevention of pain, in particular chemotherapy-induced pain.

The present invention provides a method for the treatment of pain, which comprises administering an effective amount of a compound of the present invention, or a pharmaceutically acceptable salt thereof, to a human or animal in need thereof. The present invention provides a method for the treatment or prevention of pain, which comprises administering an effective amount of a compound of the present invention, or a pharmaceutically acceptable salt thereof, to a human or animal in need thereof. The present invention also provides a method for the treatment of osteoarthritic pain, which comprises administering an effective amount of a compound of the present invention, or a pharmaceutically acceptable salt thereof, to a human or animal in need thereof.

The present invention also provides a method for the treatment or prevention of chemotherapy-induced pain, which comprises administering an effective amount of a compound of the present invention, or a pharmaceutically acceptable salt thereof, to a human or animal in need thereof.

It is preferred that the compounds of the present invention be used in the treatment of pain, in particular inflammatory pain, more particularly joint pain, most particularly osteoarthritic pain.

It is preferred that the compounds of the present invention be used in the treatment or prevention of pain, in particular chemotherapy-induced pain.

$CB_2$ receptor agonists have also been identified as having therapeutic potential in the treatment of multiple sclerosis (Br. J. Pharmacol. (2008) 153, 216-225 and J. Biol. Chem. (2008) 283, 13320-13329). Further, $CB_2$ receptor agonists have been identified as having potential for the treatment of cancer-induced bone pain (Life Sciences 86 (2010) 646-653).

Preferred species of the present invention are compounds of the formula:

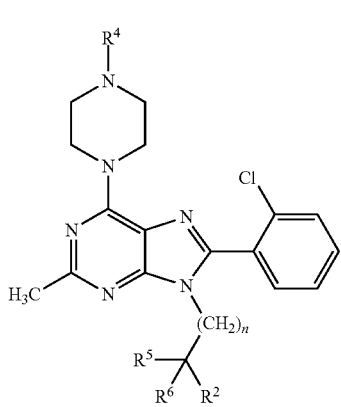

(II)

or a pharmaceutically acceptable salt thereof, wherein $R^2$, $R^4$, $R^5$, $R^6$ and n are as defined herein.

Preferred species of the present invention are compounds of the formula:

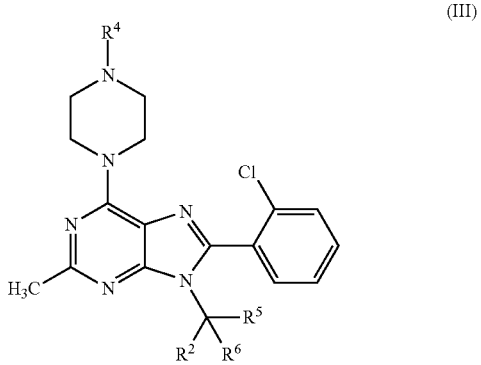

(III)

or a pharmaceutically acceptable salt thereof, wherein $R^2$, $R^4$, $R^5$ and $R^6$ are as defined herein.

Certain classes of compounds of Formula I, II or III are preferred. The following enumerated selections describe such preferred classes:

1) $R^1$ is Cl;
2) $R^2$ is OH or $CH_2OH$;
3) $R^2$ is $CH_2OH$;
4) $R^3$ is H;
5) $R^4$ is $C_1$-$C_2$ alkyl, $C_1$-$C_2$ fluoroalkyl or $C(O)CH_3$;
6) $R^4$ is methyl, ethyl, 2-fluoroethyl or $C(O)CH_3$;
7) $R^4$ is methyl or ethyl;
8) $R^5$ is H or $CH_3$;
9) $R^5$ is H;
10) $R^6$ is H or $CH_3$;
11) $R^6$ is $CH_3$;
12) n is 0;
13) $R^5$ is H and $R^6$ is $CH_3$;
14) $R^2$ is OH or $CH_2OH$; and $R^4$ is methyl, ethyl, 2-fluoroethyl or $C(O)CH_3$;
15) $R^2$ is OH or $CH_2OH$; and $R^4$ is methyl or ethyl;
16) $R^2$ is OH or $CH_2OH$; and $R^4$ is methyl;
17) $R^2$ is $CH_2OH$; $R^4$ is methyl, ethyl, 2-fluoroethyl or $C(O)CH_3$; $R^5$ is H and $R^6$ is $CH_3$.

Pharmaceutically acceptable salts of each of the compounds of the present invention are contemplated within the scope of the present application.

As used throughout this specification it is to be understood that where a group is qualified by "defined herein" or "herein defined" that said group encompasses the first occurring and broadest definition as well as each and all of the particular definitions of that group.

As used above and throughout the description of the invention, the following terms, unless otherwise indicated will have the following meaning:

As used herein the term $C_1$-$C_2$ alkyl refers to methyl or ethyl.

As used herein the term $C_1$-$C_2$ fluoroalkyl refers to a $C_1$-$C_2$ alkyl group as defined herein, wherein one or more hydrogen is replaced by fluorine and includes, trifluoromethyl, 2-fluoroethyl, 2,2-difluoroethyl and 2,2,2 trifluoroethyl. A preferred $C_1$-$C_2$ fluoroalkyl group is 2-fluoroethyl. As used herein the terms "isomer 1" and "isomer 2" relate to the specific enantiomers of final compounds or intermediates, "isomer 1" relating to the first compound to elute from the described chromatographic process and "isomer 2" the second. Where the term "isomer 1" or "isomer 2" is first attributed to an intermediate, the term is retained through to the final compound.

As used herein the term "pharmaceutically acceptable salt" refers to salts of the compounds of the present invention which are substantially non-toxic to living organisms. Such salts and common methodology for preparing them are well known in the art. See, e.g., P. Stahl, et al., Handbook of Pharmaceutical Salts: Properties Selection and Use, (VCHA/Wiley-VCH, 2002); and J. Pharm. Sci. 66, 2-19 (1977). Preferred pharmaceutically acceptable salts are hydrochloride and oxalate.

Embodiments of the invention include the examples provided herein, and although the example provided may be of one chiral or conformational form, or a salt thereof, further embodiments of the invention include all other stereoisomeric and or conformational forms of the examples described, as well as pharmaceutically acceptable salts thereof.

As used herein the term "$CB_2$-selective agonists" or "$CB_2$-selectivity" refers to compounds having greater potency at $CB_2$ than $CB_1$. Preferably compounds of the present invention exhibit ≥100 fold $CB_2$-selectivity. More preferably compounds of the present invention exhibit ≥500 fold $CB_2$-selectivity. Most preferably compounds of the present invention exhibit ≥1000 fold $CB_2$-selectivity.

The compounds of the present invention are preferably formulated as pharmaceutical compositions administered by a variety of routes. Preferably, such compositions are for oral administration. Such pharmaceutical compositions and processes for preparing same are well known in the art. See, e.g., Remington: The Science and Practice of Pharmacy (A. Gennaro, et al., eds., 19th ed., Mack Publishing Co., 1995).

X-Ray Diffraction (XRD) patterns of the compounds of the invention may be obtained on a Bruker D4 Endeavor® X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. Peak position variability of ±0.2 in 2θ will take into account potential variations without hindering the unequivocal identification of the indicated crystal form.

A preferred compound of the present invention is 2-[8-(2-Chloro-phenyl)-2-methyl-6-(4-methyl-piperazin-1-yl)-purin-9-yl]-propan-1-ol; a more preferred compound is (2R)-2-[8-(2-chlorophenyl)-2-methyl-6-(4-methylpiperazin-1-yl)purin-9-yl]propan-1-ol.

A preferred form of (2R)-2-[8-(2-chlorophenyl)-2-methyl-6-(4-methylpiperazin-1-yl)purin-9-yl]propan-1-ol is characterized by XRD having a diffraction peak (2-theta values) at 8.26 in combination with one or more of the peaks selected from 19.68, 14.81, and 13.20; ±0.2°; preferably having diffraction peaks at 8.26, and 19.68 in combination with one or more of the peaks selected from 14.81, and 13.20; ±0.2°.

The following Schemes, Preparations, and Examples are provided to better elucidate the practice of the present invention. Suitable reaction conditions for the steps of these Schemes, Preparations, and Examples are well known in the art and appropriate modification of reaction conditions, including substitution of solvents and co-reagents are within the ability of the skilled artisan.

Furthermore, the skilled artisan will appreciate that in some circumstances, the order in which moieties are introduced is not critical. The particular order of steps required to produce the compounds of Formula I is dependent upon the particular compound being synthesized, the starting compound, and the relative lability of the substituted moieties, as is well appreciated by the skilled chemist. The skilled artisan will appreciate that not all substituents are compatible with all reaction conditions. These compounds may be protected or modified at a convenient point in the synthesis by methods well known in the art.

Suitable protecting groups include those described in T. W. Greene, "Protective Groups in Organic Synthesis", John Wiley and Sons, New York, N.Y., 1991, hereafter referred to as "Greene". Greene indicates appropriate conditions for "protection" and "de-protection" of suitable protecting groups to be used by the skilled artisan.

The intermediates and final products of the present invention may be further purified, if desired by common techniques such as recrystallization or chromatography over solid supports such as silica gel or alumina The names for the compounds of the present invention are generated using Symyx Version 3.1.NET with the IUPAC naming functionality.

Abbreviations used herein are defined as follows: "Brine" means a saturated aqueous sodium chloride solution; "BSA" means bovine serum albumin; "DCM" means dichloromethane; "DDQ" means 2,3-dichloro-5,6-dicyano-1,4-benzoquinone; "DMAC" means N,N-dimethylacetamide; "DMF" means N,N-dimethylformamide; "EDTA" means ethylenediaminetetraacetic acid; "EtOAc" means ethyl acetate; "GDP" means guanosine diphosphate; "HEPES" means 4-(2-hydroxyethyl)-1-piperazineethanesulfonic acid; "IPA" means 2-propanol; "IPAm" means 2-propylamine; "MeOH" means methanol; "SCX" means a silica based strong cation exchange resin column, disposable cartridge or equivalent; "SFC" means supercritical fluid chromatography; "THF" means tetrahydrofuran; "tBOC" means tert-butoxycarbonyl.

Scheme 1

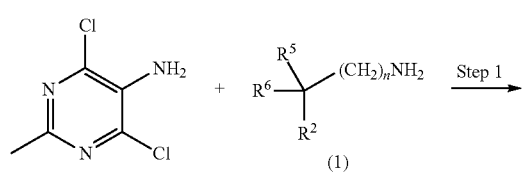

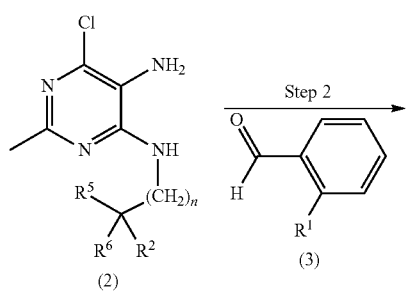

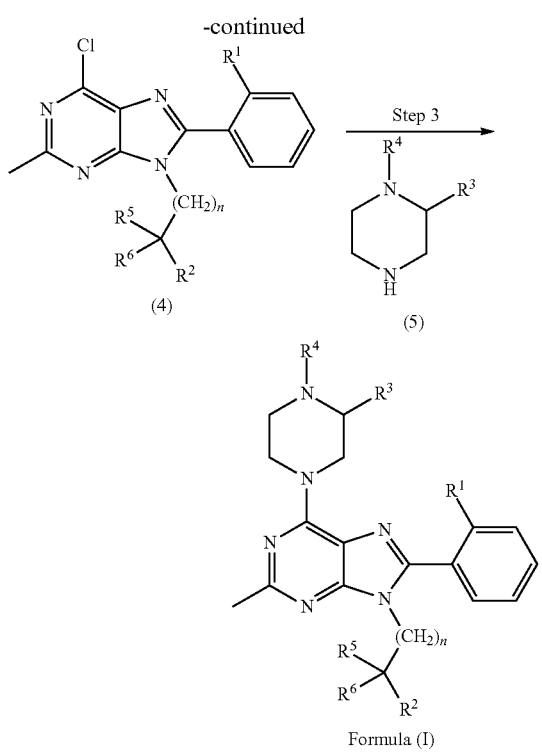

A compound of Formula (I) can be prepared in accordance with reactions as depicted in Scheme 1.

In Step 1, 4,6-dichloro-2-methyl-pyrimidin-5-ylamine is reacted with an amine (1) in a displacement reaction to provide a diamino pyrimidine (2). The reaction can proceed in the presence of a suitable base, such as triethylamine or diisopropylethylamine, in a suitable solvent such as isopropanol, at an elevated temperature such as about 100 to 160° C., preferably in a sealed tube. Alternatively the reaction can be accomplished using microwave irradiation.

In Step 2, an imine is formed from the diamino pyrimidine (2) and a benzaldehyde (3) in the presence of an acid catalyst such as ferric chloride on silica, or p-toluenesulfonic acid. The reaction takes place in a suitable solvent such as 1,4-dioxane or toluene, at an elevated temperature such as about 70° C. to 110° C. In the absence of silica, molecular sieves can be added to remove water from the reaction. After filtration to remove the solids and concentration, the oxidative cyclization of the imine can be accomplished in a suitable solvent such as dichloromethane, in the presence of an oxidate such as DDQ, at a suitable temperature such as about −30 to 40° C. to give a 6-chloropurine of formula (4).

In Step 3, a 6-chloropurine (4) undergoes a displacement reaction with a piperazine (5) to provide a piperazinyl purine of Formula (I). The reaction can proceed in the presence of a suitable base, such as triethylamine or diisopropylethylamine, in a solvent such as methanol, ethanol, or isopropanol, at an elevated temperature such as about 50 to 100° C. Alternatively the reaction can be accomplished using microwave irradiation.

It will be recognized by one skilled in the art that the amine functionality present in the piperazinyl moiety, can be protected with a suitable protecting group such as tBOC. After the displacement in Step 3, the protecting group can be subsequently removed and the amine acylated or alkylated to make further compounds of Formula (I).

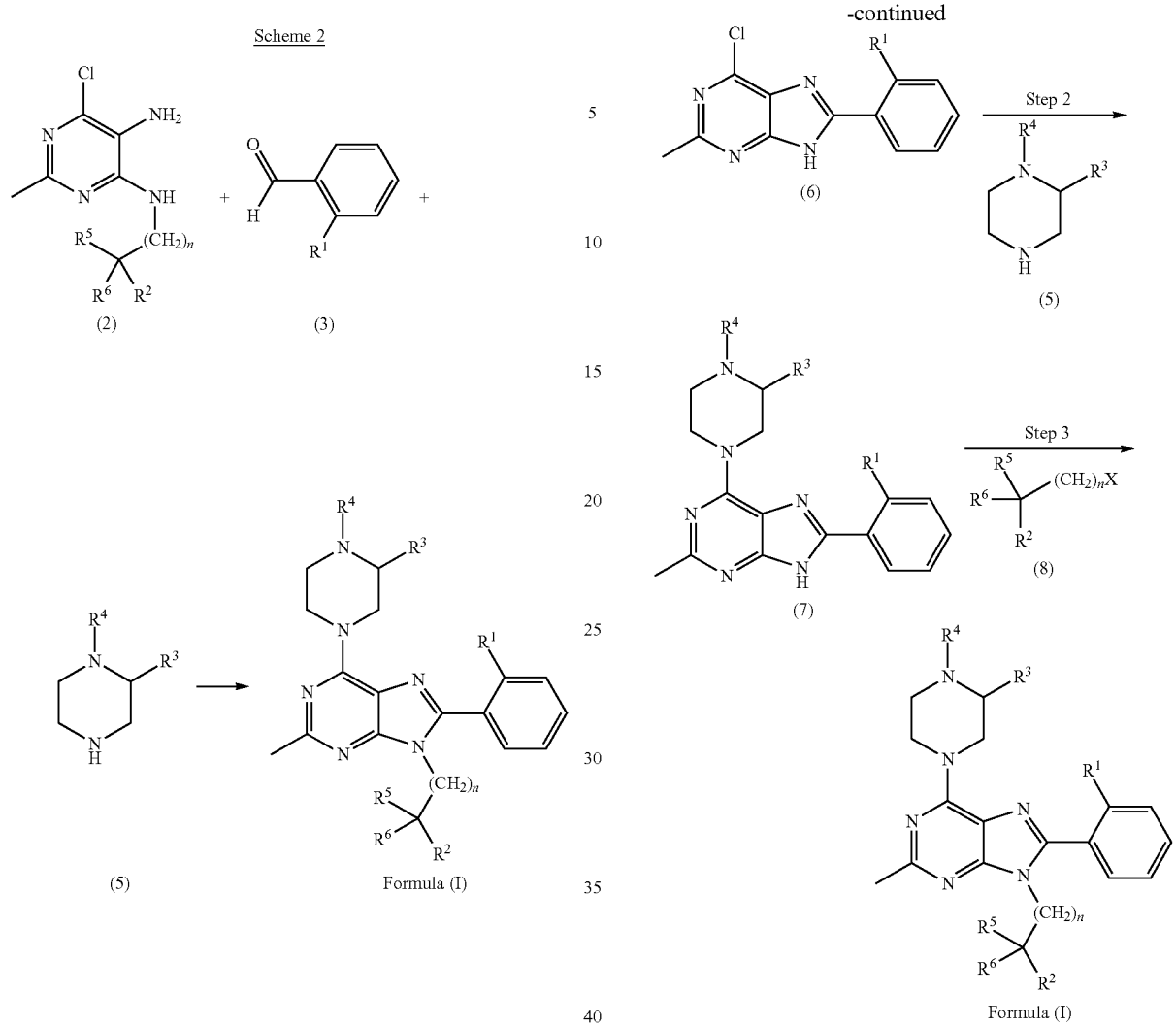

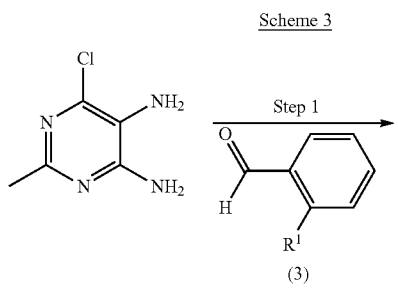

In Scheme 2 is depicted an alternative method for obtaining a compound of Formula (I).

A diamino pyrimidine (2) is combined together with a benzaldehyde (3) and a piperazine (5) in the presence of a suitable oxidant, such as nitrobenzene or acetic acid. The reaction is performed in a suitable solvent, such as methoxybenzene, at an elevated temperature such as about 120 to 150° C., with the reaction open to the atmosphere, to provide a compound of Formula (I).

In Scheme 3 is depicted another alternative for making a compound of Formula (I).

In Step 1, 6-chloro-2-methyl-4,5-pyrimidinediamine is reacted with a benzaldehyde (3) to provide a 6-chloropurine (6), essentially as described in Scheme 1, Step 2, above. In Step 2, a 6-chloropurine (6) is reacted with a piperazine (5) to provide a piperazinyl purine (7) essentially as described in Scheme 1, Step 3, above.

In Step 3, a piperazinyl purine (7) is alkylated with a haloalkane (8) (wherein X=Br or I) to give a compound of Formula (I). It will be appreciated by the skilled artisan that there are various methods to accomplish such alkylations. For example, the piperazinyl purine (7) can be treated with a suitable base such as sodium hydride, potassium hydride, cesium or potassium carbonate, or sodium or potassium bis(trimethylsilyl)amide. Suitable solvents include inert solvents such as THF, dioxane, DMF, DMAC, or N-methyl-2-pyrrolidinone. Preferred conditions use sodium hydride, in THF, at a suitable temperature such as about −70 to 50° C. to provide a compound of Formula (I). It will be recognized by one skilled in the art that compounds of Formula (I) wherein $R^2$ contains a terminal alcohol, can be protected during the alkylation step by use of a suitable protecting group and subsequently removal of the protecting group.

Scheme 4

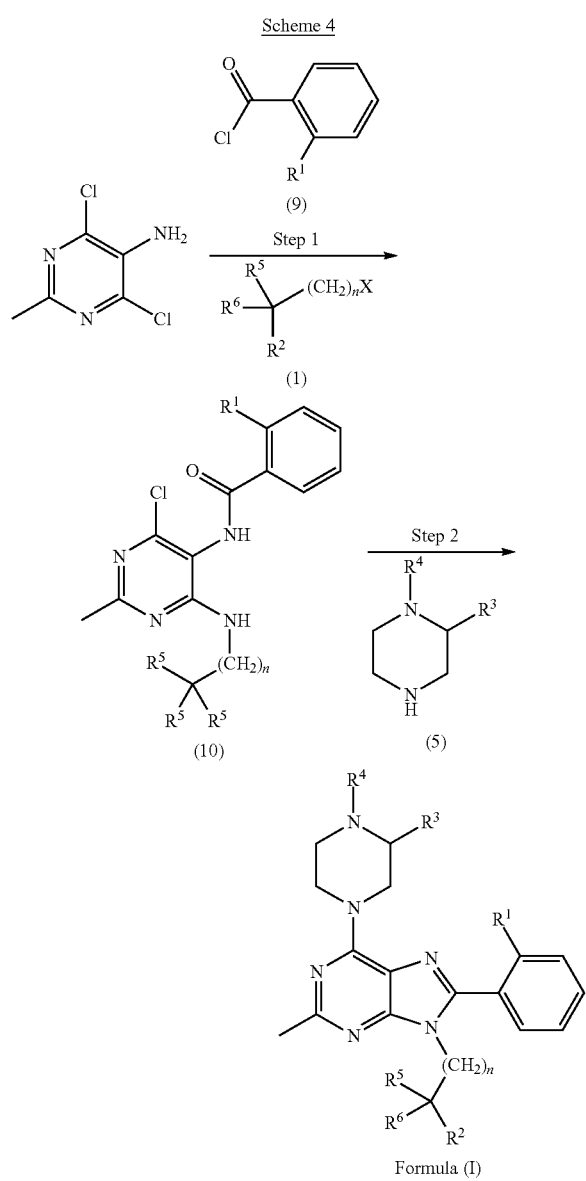

In Scheme 4 is depicted yet another alternative for making a compound of Formula (I).

In Step 1, 5-amino-4,6-dichloro-2-methylpyrimidine is acylated with a benzoyl chloride (9) followed by displacement with an amine (1) to provide an amino amido pyrimidine (10). The reaction is accomplished in an inert solvent such as dimethyl acetamide or N-methyl-2-pyrrolidone at an elevated temperature such as 60 to 100° C. in the presence of a benzoyl chloride (9). Water is added and heating continued before adding a suitable organic base such as diisopropylethylamine or triethylamine. This is followed by addition of an amine (1) with continued heating.

In Step 2, the amino amido pyrimidine (10) is combined with a piperazine (5) in a sealed vessel to provide a compound of Formula (I). The reaction takes place in a suitable solvent such as isopropanol, at an elevated temperature such as 140 to 180° C. in the presence of a suitable organic base, such as diisopropylethylamine Preparation 1

6-Chloro-N4-(2-methoxyethyl)-2-methylpyrimidine-4,5-diamine

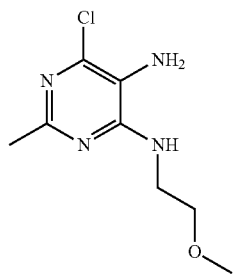

Heat a solution of 4,6-dichloro-2-methyl-pyrimidin-5-ylamine (5.0 g, 0.02 mol), 2-methoxyethylamine (2.32 g, 0.03 mol) and diisopropylethylamine (3.9 g, 0.03 mol) in isopropanol (70 mL) at 150° C. in a sealed tube for 16 h. Cool the reaction mixture to room temperature, and remove the isopropanol under reduced pressure to give a residue. Dissolve the residue in dichloromethane and wash with water and brine. Dry the organic layer over anhydrous sodium sulfate, filter, and concentrate under reduced pressure to give a residue. Purify the residue on a silica gel column eluting with methanol:dichloromethane (4:96) to give the title compound (5.0 g). ES/MS m/z 217 (M+1).

Prepare the diamino pyrimidines in the table below by essentially following the procedure as described in Preparation 1, using the appropriate amine and 4,6-dichloro-2-methyl-pyrimidin-5-ylamine. Purify Preparations 3, 4, and 7 using silica gel chromatography, eluting with ethyl acetate/hexane. Purify Preparation 9 using silica gel chromatography, eluting with acetone/hexane. Purify Preparation 10 using Biotage Isolute® SCX-2 (propylsulfonic acid functionalized silica) with $NH_3$ 7 M in MeOH as eluent.

| Prep | Chemical name | Structure | ES/MS m/z |
|---|---|---|---|
| 2 | 6-Chloro-2-methyl-pyrimidine-4,5-diamine | 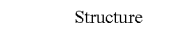 | 159 (M + 1) |

-continued
| Prep | Chemical name | Structure | ES/MS m/z |
|---|---|---|---|
| 3 | 6-Chloro-N4-(3-methoxypropyl)-2-methyl-pyrimidine-4,5-diamine | 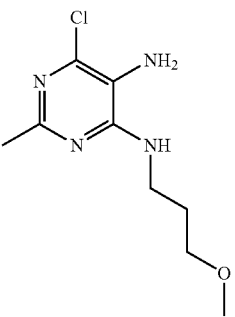 | 231 (M + 1) |
| 4 | 6-Chloro-N4-(2-methoxy-2-methyl-propyl)-2-methyl-pyrimidine-4,5-diamine | 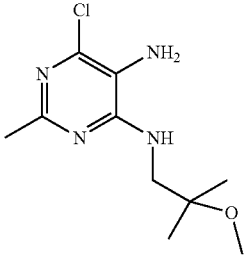 | 245 (M + 1) |
| 5 | 1-[(5-Amino-6-chloro-2-methyl-pyrimidin-4-yl)amino]-2-methyl-propan-2-ol | 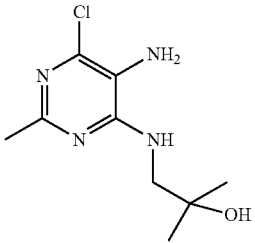 | 231 (M + 1) |
| 6 | 3-[(5-Amino-6-chloro-2-methyl-pyrimidin-4-yl)amino]-2,2-dimethyl-propan-1-ol | 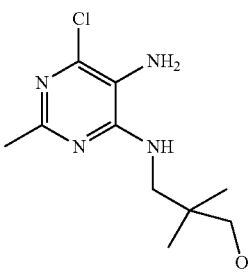 | 245 (M + 1) |
| 7 | 1-[(5-Amino-6-chloro-2-methyl-pyrimidin-4-ylamino)-methyl]-cyclopropanol | 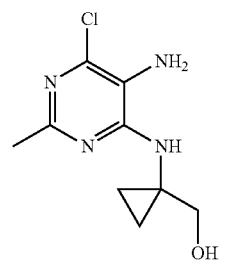 | 229 (M + 1) |

-continued

| Prep | Chemical name | Structure | ES/MS m/z |
|---|---|---|---|
| 8 | 1-(5-Amino-6-chloro-2-methyl-pyrimidin-4-ylamino)-2-methyl-propan-2-ol | 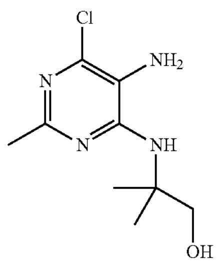 | 231 (M + 1) |
| 9 | 2-(5-Amino-6-chloro-2-methyl-pyrimidin-4-ylamino)-propan-1-ol | 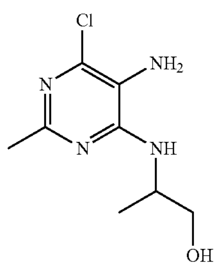 | 217 (M + 1) |
| 10 | 6-Chloro-N*4*-(2-methoxy-1-methoxymethyl-ethyl)-2-methyl-pyrimidine-4,5-diamine | 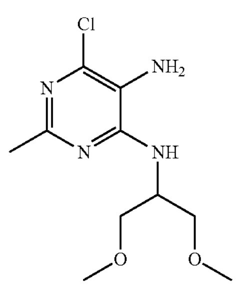 | 261 (M + 1) |

Preparation 11

6-Chloro-8-(2-chlorophenyl)-9-(2-methoxyethyl)-2-methyl-purine

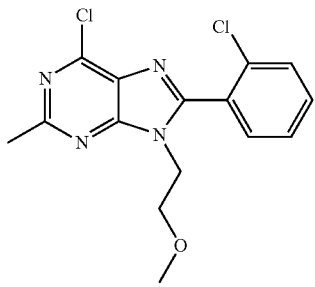 [SMILES: COCCn1c(-c2ccccc2Cl)nc2c(Cl)nc(C)nc21]

Heat a solution of 6-chloro-N4-(2-methoxyethyl)-2-methylpyrimidine-4,5-diamine (5.0 g, 0.023 mol), 2-chlorobenzaldehyde (4.8 g, 0.03 mol), 15% FeCl$_3$ on SiO$_2$ (20 g) in 1,4-dioxane (150 mL) to 100° C. for 16 h. Remove the silica by filtration through diatomaceous earth, and concentrate the filtrate under reduced pressure to give a residue. Dissolve the residue in dry dichloromethane (150 mL) and add DDQ (5.2 g, 0.022 mol) at 0° C., and stir the reaction mixture at room temperature for 2 h. Dilute the reaction mixture with dichloromethane, wash with 1 N sodium hydroxide solution, water, and brine. Dry the organic layer over anhydrous sodium sulfate, filter, and concentrate to give a residue. Purify the residue on a silica gel column eluting with ethyl acetate:n-hexane (40:60) to give the title compound (2.9 g). ES/MS m/z 337 (M+1).

Prepare the phenylpurines in the table below by essentially following the procedure as described in Preparation 11, using the appropriate diamino pyrimidine and 2-chlorobenzaldehyde or 2-methylbenzaldehyde. Purify Preparation 17 using silica gel chromatography with acetone/hexane as eluent.

| Prep | Chemical name | Structure | ES/MS m/z |
|---|---|---|---|
| 12 | 6-Chloro-8-(2-chlorophenyl)-2-methyl-9H-purine | 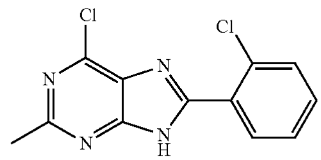 [SMILES: Cc1nc(Cl)c2nc(-c3ccccc3Cl)[nH]c2n1] | 279 (M + 1) |
| 13 | 6-Chloro-8-(2-chlorophenyl)-9-(3-methoxypropyl)-2-methyl-purine | 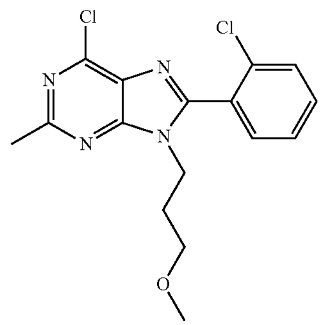 [SMILES: COCCCn1c(-c2ccccc2Cl)nc2c(Cl)nc(C)nc21] | 351 (M + 1) |
| 14 | 6-Chloro-8-(2-chlorophenyl)-9-(2-methoxy-2-methyl-propyl)-2-methyl-purine | 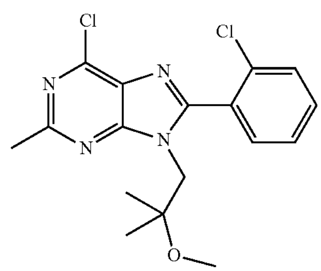 [SMILES: COC(C)(C)Cn1c(-c2ccccc2Cl)nc2c(Cl)nc(C)nc21] | 365 (M + 1) |
| 15 | 2-[6-Chloro-2-methyl-8-(o-tolyl)purin-9-yl]ethanol | 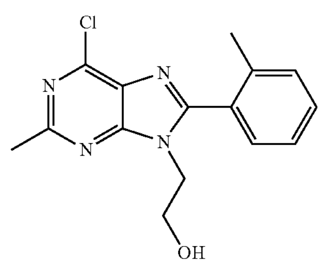 [SMILES: Cc1nc(Cl)c2nc(-c3ccccc3C)n(CCO)c2n1] | 303 (M + 1) |
| 16 | 2-[6-Chloro-8-(2-chlorophenyl)-2-methyl-purin-9-yl]-2-methyl-propan-1-ol | 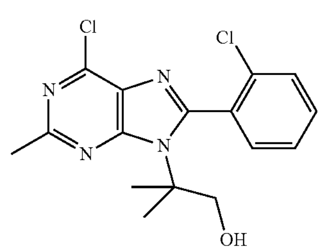 [SMILES: Cc1nc(Cl)c2nc(-c3ccccc3Cl)n(C(C)(C)CO)c2n1] | 351 (M + 1) |
| 17 | (±) 2-[6-Chloro-8-(2-chlorophenyl)-2-methyl-purin-9-yl]propan-1-ol | 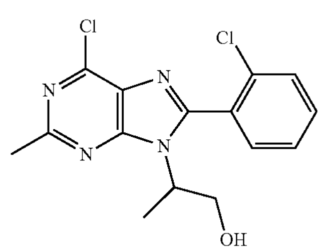 [SMILES: Cc1nc(Cl)c2nc(-c3ccccc3Cl)n(C(C)CO)c2n1] | 337 (M + 1) |

Preparation 18

1-(6-Chloro-8-(2-chlorophenyl)-2-methyl-purin-9-yl)-2-methyl-propan-2-ol

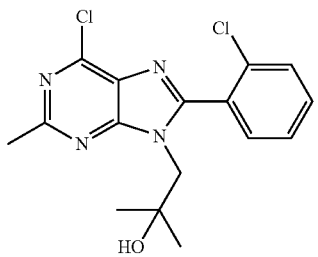 [SMILES: Cc1nc(Cl)c2nc(-c3ccccc3Cl)n(C(C)C(C)(C)O)c2n1]

Heat a mixture of 1-(5-amino-6-chloro-2-methylpyrimidin-4-ylamino)-2-methylpropan-2-ol (0.5 g, 0.002 mol), 2-chlorobenzaldehyde (0.6 g, 0.004 mol), p-toluene sulfonic acid (0.1 g) and molecular sieves (1.0 g) in toluene (25 mL) to 130° C. for 16 h. Remove the molecular sieves by filtration through diatomaceous earth, and concentrate the filtrate under reduced pressure to give a residue. Dissolve the residue in dry dichloromethane (5 mL) and add DDQ (0.47 g, 0.002 mol) at 0° C. Stir the reaction mixture at room temperature for 2 h. Dilute the reaction mixture with dichloromethane, wash with 1 N sodium hydroxide solution, water, and brine. Dry the organic layer over anhydrous sodium sulfate, filter, and concentrate to give a residue. Purify the residue on a silica gel column eluting with methanol:dichloromethane (2:98) to give the title compound (0.4 g). ES/MS m/z 351 (M+1).

Prepare the phenylpurine in the table below by essentially following the procedure as described in Preparation 18, using 3-[(5-amino-6-chloro-2-methyl-pyrimidin-4-yl)amino]-2,2-dimethyl-propan-1-ol and 2-chlorobenzaldehyde.

| Prep | Chemical name | Structure | ES/MS m/z |
|---|---|---|---|
| 19 | 3-[6-Chloro-8-(2-chlorophenyl)-2-methyl-purin-9-yl]-2,2-dimethyl-propan-1-ol | 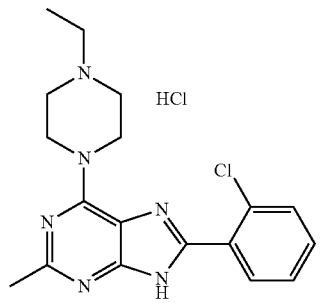 | 365 (M + 1) |

Preparation 20

1-(2-Fluoroethyl)piperazine dihydrochloride

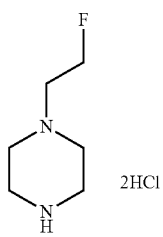

Charge a reaction vessel with N-tert-butoxycarbonylpiperazine (1.600 g, 8.590 mmol), potassium carbonate (3.56 g, 25.77 mmol), sodium iodide (catalytic) (10 mg, 66.7 mmol), 1,4-dioxane (20 mL), and 1-bromo-2-fluoroethane (704.0 μL, 9.45 mmol). Heat the mixture with stirring at reflux temperature overnight. Upon reaction completion, cool to room temperature and concentrate under reduced pressure. Partition the resulting residue with ethyl acetate and water. Separate the organic layer and dry over anhydrous sodium sulfate, filter, and concentrate under reduced pressure to afford pure 4-(2-fluoro-ethyl)-piperazine-1-carboxylic acid tert-butyl ester. GC-MS m/z 232 (M).

Add 4 N HCl in 1,4-dioxane (21.52 mL, 86.1 mmol) to a stirred solution of 4-(2-fluoro-ethyl)-piperazine-1-carboxylic acid tert-butyl ester (2.00 g, 8.61 mmol) in dry dichloromethane (60 mL) at room temperature under nitrogen. Stir overnight under nitrogen. Concentrate the reaction under reduced pressure to afford the title compound (1.78 g). ES/MS m/z 133 (M+1).

Preparation 21

8-(2-Chlorophenyl)-6-(4-ethylpiperazin-1-yl)-2-methyl-9H-purine hydrochloride Heat a solution of 6-chloro-8-(2-chloro-phenyl)-2-methyl-9H-purine (0.5 g, 0.0017 mol), N-ethyl piperazine (0.22 g, 0.0019 mol), and triethyl amine (0.22 g, 0.0022 mol) in ethanol (10 mL) at 90° C. for 8 h. Alternatively, heat the reaction with microwave irradiation. Upon reaction completion, concentrate the reaction mixture under reduced pressure. Dissolve the residue in dry dichloromethane and wash with saturated sodium bicarbonate solution, water, and brine. Dry the organic layer over anhydrous sodium sulfate, filter, and concentrate under reduced pressure to give a residue. Purify the residue on a silica gel column using MeOH:DCM (2:98) as eluent to give 8-(2-Chlorophenyl)-6-(4-ethylpiperazin-1-yl)-2-methyl-9H-purine (0.25 g). Add HCl (2 M solution in ethanol) (1.0 eq) into the mixture of 8-(2-chlorophenyl)-6-(4-ethylpiperazin-1-yl)-2-methyl-9H-purine (0.25 g, 0.0007 mol) in dry ether (2.5 mL) at 0° C. and stir for one hour at room temperature. Filter the precipitate, wash with ether and DCM. Dry under vacuum to give the title compound (0.275 g) as a white solid. ES/MS m/z 357 (M+1).

Alternatively, prepare the HCl salt by dissolving the free base in acetone, 1:1 acetonitrile:water, or another suitable organic solvent, then add with stirring a solution of aqueous or ethereal HCl. Then lyophilize to afford the hydrochloride salt.

Prepare the phenyl piperazinylpurines in the table below by essentially following the procedure as described in Preparation 21, using the appropriately substituted piperazine and substituted 6-chloropurine. Unless otherwise noted purify free base products using normal phase silica gel chromatography with acetone/hexane or MeOH/DCM as eluent.

| Ex or Prep | Chemical name | Structure | ES/MS m/z |
|---|---|---|---|
| Prep 22 | tert-Butyl 4-[8-(2-chlorophenyl)-9-(2-hydroxy-2-methyl-propyl)-2-methyl-purin-6-yl]piperazine-1-carboxylate | 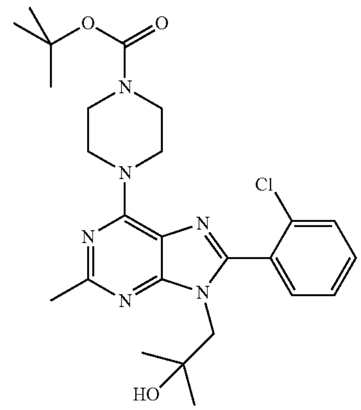 [SMILES: Cc1nc(N2CCN(C(=O)OC(C)(C)C)CC2)c2nc(-c3ccccc3Cl)n(CC(C)(C)O)c2n1] | 501 (M + 1) |
| Ex 1 | 8-(2-Chlorophenyl)-6-(4-ethylpiperazin-1-yl)-9-(2-methoxyethyl)-2-methyl-purine hydrochloride | 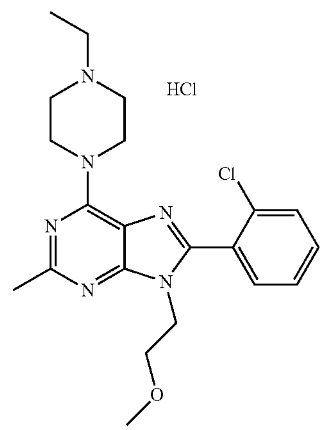 [SMILES: CCN1CCN(c2nc(C)nc3c2nc(-c2ccccc2Cl)n3CCOC)CC1 ; Cl] | 415 (M + 1) |
| Ex 2 | 8-(2-Chlorophenyl)-6-[4-(2-fluoroethyl)piperazin-1-yl]-9-(2-methoxyethyl)-2-methyl-purine hydrochloride | 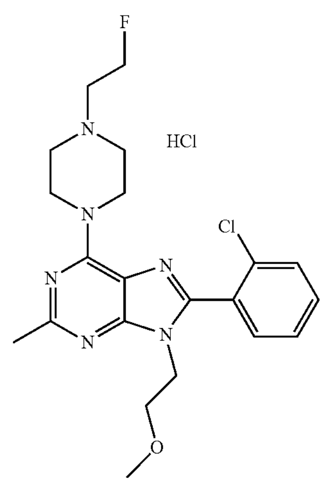 [SMILES: COCCn1c(-c2ccccc2Cl)nc2c(N3CCN(CCF)CC3)nc(C)nc21 ; Cl] | 433 (M + 1) |

-continued
| Ex or Prep | Chemical name | Structure | ES/MS m/z |
|---|---|---|---|
| Ex 3 | 1-[4-[8-(2-Chlorophenyl)-9-(2-methoxyethyl)-2-methyl-purin-6-yl]piperazin-1-yl]ethanone hydrochloride | 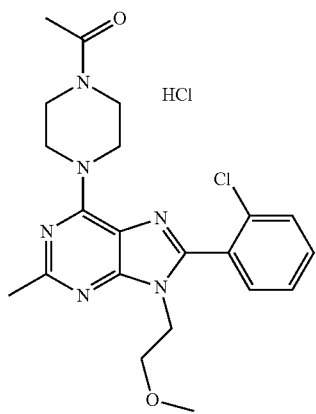 [SMILES: COCCn1c(-c2ccccc2Cl)nc2c(N3CCN(C(C)=O)CC3)nc(C)nc21 ; Cl] | 429 (M + 1) |
| Ex 4 | 8-(2-Chlorophenyl)-6-(4-ethylpiperazin-1-yl)-9-(3-methoxypropyl)-2-methyl-purine hydrochloride | 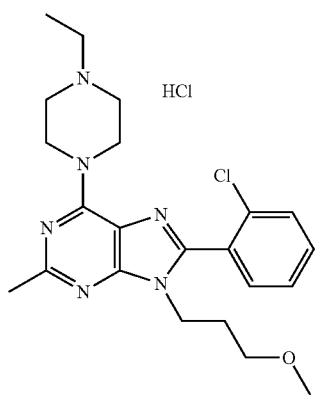 [SMILES: CCN1CCN(c2nc(C)nc3c2nc(-c2ccccc2Cl)n3CCCOC)CC1 ; Cl] | 429 (M + 1) |
| Ex 5 | 1-[4-[8-(2-Chlorophenyl)-9-(3-methoxypropyl)-2-methyl-purin-6-yl]piperazin-1-yl]ethanone hydrochloride | 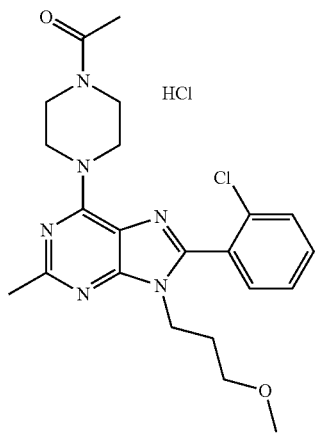 [SMILES: COCCCn1c(-c2ccccc2Cl)nc2c(N3CCN(C(C)=O)CC3)nc(C)nc21 ; Cl] | 443 (M + 1) |

-continued
| Ex or Prep | Chemical name | Structure | ES/MS m/z |
|---|---|---|---|
| Ex 6 | 8-(2-Chlorophenyl)-6-[4-(2-fluoroethyl)piperazin-1-yl]-9-(3-methoxypropyl)-2-methyl-purine hydrochloride | 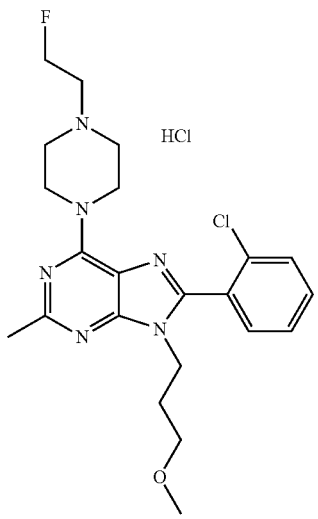 [SMILES: COCCCn1c(-c2ccccc2Cl)nc2c(N3CCN(CCF)CC3)nc(C)nc21 ; Cl] | 447 (M + 1) |
| Ex 7 | 8-(2-Chlorophenyl)-6-(4-ethylpiperazin-1-yl)-9-(2-methoxy-2-methyl-propyl)-2-methyl-purine hydrochloride | 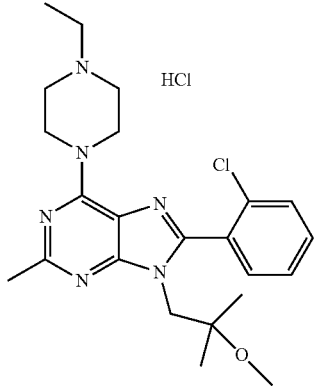 [SMILES: CCN1CCN(c2nc(C)nc3c2nc(-c2ccccc2Cl)n3CC(C)(C)OC)CC1 ; Cl] | 443 (M + 1) |
| Ex 8 | 1-[4-[8-(2-Chlorophenyl)-9-(2-methoxy-2-methyl-propyl)-2-methyl-purin-6-yl]piperazin-1-yl]ethanone | 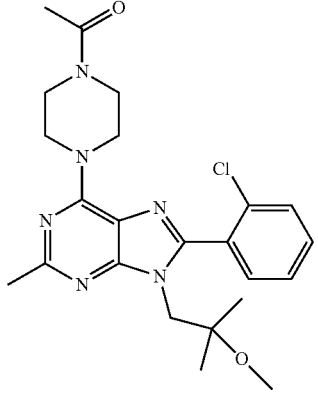 [SMILES: COC(C)(C)Cn1c(-c2ccccc2Cl)nc2c(N3CCN(C(C)=O)CC3)nc(C)nc21] | 457 (M + 1) |

-continued

| Ex or Prep | Chemical name | Structure | ES/MS m/z |
|---|---|---|---|
| Ex 9 | 2-[8-(2-Chlorophenyl)-2-methyl-6-(4-methylpiperazin-1-yl)purin-9-yl]ethanol hydrochloride | 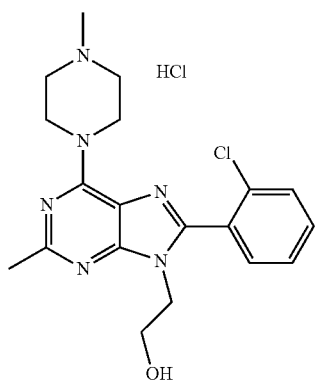 [SMILES: Cc1nc(N2CCN(C)CC2)c2nc(-c3ccccc3Cl)n(CCO)c2n1 ; Cl] | 387 (M + 1) |
| Ex 10 | 1-[4-[9-(2-Hydroxyethyl)-2-methyl-8-(o-tolyl)purin-6-yl]piperazin-1-yl]ethanone hydrochloride | 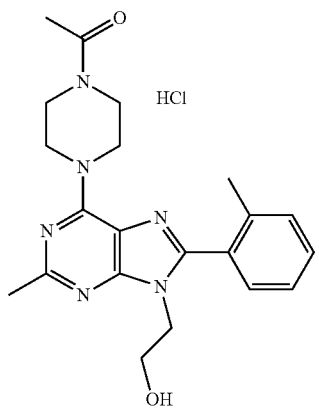 [SMILES: CC(=O)N1CCN(c2nc(C)nc3c2nc(-c2ccccc2C)n3CCO)CC1 ; Cl] | 395 (M + 1) |
| Ex 11 | 2-[2-Methyl-6-(4-methylpiperazin-1-yl)-8-(o-tolyl)purin-9-yl]ethanol hydrochloride | 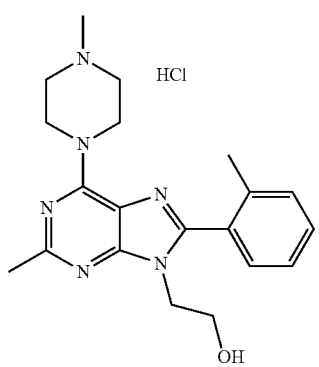 [SMILES: Cc1nc(N2CCN(C)CC2)c2nc(-c3ccccc3C)n(CCO)c2n1 ; Cl] | 367 (M + 1) |
| Ex 12 | 1-[8-(2-Chlorophenyl)-2-methyl-6-(4-methylpiperazin-1-yl)purin-9-yl]-2-methyl-propan-2-ol hydrochloride | 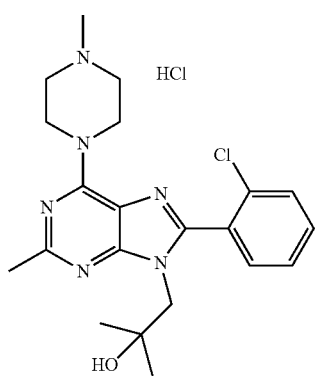 [SMILES: Cc1nc(N2CCN(C)CC2)c2nc(-c3ccccc3Cl)n(CC(C)(C)O)c2n1 ; Cl] | 415 (M + 1) |

-continued

| Ex or Prep | Chemical name | Structure | ES/MS m/z |
|---|---|---|---|
| Ex 13 | 1-[4-[8-(2-Chlorophenyl)-9-(2-hydroxy-2-methyl-propyl)-2-methyl-purin-6-yl]piperazin-1-yl]ethanone hydrochloride | 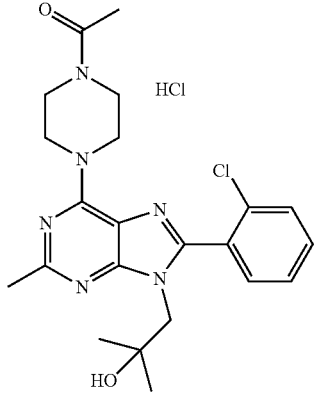 [SMILES: CC(=O)N1CCN(c2nc(C)nc3c2nc(-c2ccccc2Cl)n3CC(C)(C)O)CC1 ; Cl] | 443 (M + 1) |
| Ex 14 | 3-[8-(2-Chlorophenyl)-2-methyl-6-(4-methylpiperazin-1-yl)purin-9-yl]-2,2-dimethyl-propan-1-ol hydrochloride | 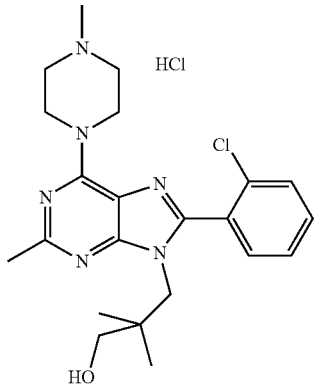 [SMILES: Cc1nc(N2CCN(C)CC2)c2nc(-c3ccccc3Cl)n(CC(C)(C)CO)c2n1 ; Cl] | 429 (M + 1) |
| Ex 15 | 2-[8-(2-Chloro-phenyl)-2-methyl-6-(4-methyl-piperazin-1-yl)-purin-9-yl]-2-methyl-propan-1-ol hydrochlorides | 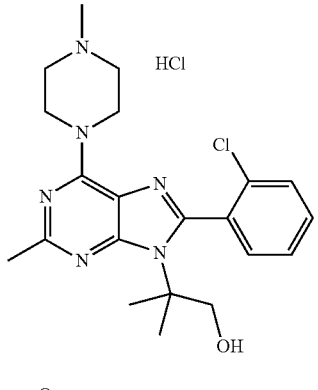 | 415 (M + 1) |
| Ex 16 | 1-{4-[8-(2-Chloro-phenyl)-9-(2-hydroxy-1-methyl-ethyl)-2-methyl-9H-purin-6-yl]-piperazin-1-yl}-ethanone hydrochloride, Isomer 1[b] | 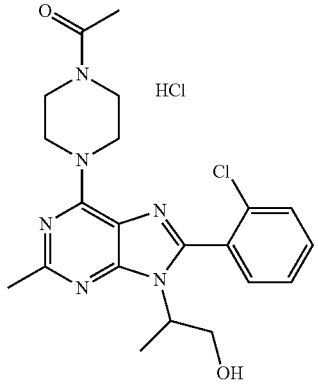 [SMILES: CC(=O)N1CCN(c2nc(C)nc3c2nc(-c2ccccc2Cl)n3C(C)CO)CC1 ; Cl] | 429 (M + 1) |

-continued

| Ex or Prep | Chemical name | Structure | ES/MS m/z |
|---|---|---|---|
| Ex 17 | 1-{4-[8-(2-Chloro-phenyl)-9-(2-hydroxy-1-methyl-ethyl)-2-methyl-9H-purin-6-yl]-piperazin-1-yl}-ethanone hydrochloride, Isomer 2[b] | 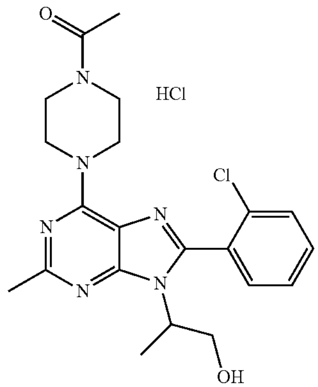 [SMILES: CC(=O)N1CCN(c2nc(C)nc3c2nc(-c2ccccc2Cl)n3C(C)CO)CC1 ; Cl] | 429 (M + 1) |
| Ex 18 | 2-[8-(2-Chloro-phenyl)-2-methyl-6-(4-methyl-piperazin-1-yl)-purin-9-yl]-propan-1-ol hydrochloride, Isomer 1[c] | 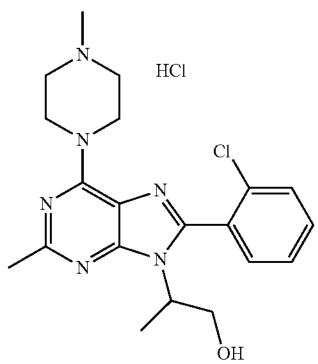 [SMILES: Cc1nc(N2CCN(C)CC2)c2nc(-c3ccccc3Cl)n(C(C)CO)c2n1 ; Cl] | 401 (M + 1) |
| Ex 19 | 2-[8-(2-Chloro-phenyl)-2-methyl-6-(4-methyl-piperazin-1-yl)-purin-9-yl]-propan-1-ol hydrochloride, Isomer 2[c] | 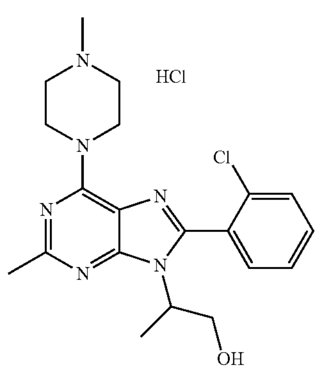 [SMILES: Cc1nc(N2CCN(C)CC2)c2nc(-c3ccccc3Cl)n(C(C)CO)c2n1 ; Cl] | 401 (M + 1) |

[a]Reverse phase Preparative HPLC, Waters ® xbridge, Eluent: 9 to 100% Acetonitrile/Water pH10 (NH$_4$CO$_3$).
[b]Purify by chiral separation: Diacel OJ-H SFC, Eluent: 12% MeOH (0.2% IPAm)/CO$_2$. Isomer 1 (100% ee) and Isomer 2 (91.1% ee).
[c]Purify by chiral separation: Diacel AD-H SFC, Eluent: 10% IPA(0.2% diethylmethylamine)/CO$_2$. Isomer 1 (100% ee) and Isomer 2 (100% ee).

Preparation 23

(2R)-2-[(5-Amino-6-chloro-2-methyl-pyrimidin-4-yl)amino]propan-1-ol

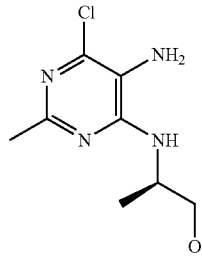

Charge 4,6-dichloro-2-methyl-pyrimidin-5-ylamine (307 g, 1.72 moles) into a 10 L flange flask mounted on an isomantle equipped with an overhead stirrer, reflux coil condenser, thermometer, and addition funnel. Then add isopropyl alcohol (3.45 L) to the flask and stir to give a clear pale yellow solution. Add triethylamine (456.7 mL, 3.28 mol) to the flask in one portion while stirring and warm to 50° C. Slowly add (R)-(−)-2-amino-1-propanol (194.30 g, 202.10 mL, 2.59 mol) from the addition funnel over 30 min. After the final addition heat the reaction mixture at reflux for 36 h. Allow the reaction mixture to cool. Add additional (R)-(−)-2-amino-1-propanol (64.77 g, 67.37 mL, 862.26 mmol, 0.5 eq) and triethylamine (174.51 g, 240.37 mL, 1.72 moles, 1.0 eq) to the reaction mixture and reflux for 18 h. Allow the reaction mixture to cool. Add additional (R)-(−)-2-amino-1-propanol (32.38 g, 33.68 mL, 431.13 mmol, 0.25 eq) and triethylamine (87.25 g, 120.18 mL, 862.26 mmol, 0.5 eq) to the reaction mixture and heat to reflux for 6 h. Allow to cool while stirring at ambient temperature for 48 h.

Remove the solvent by rotary evaporation to provide an off white semi-solid. Add water (500 mL) and remove residual iso-propanol from the resulting white slurry by rotary evaporation. Collect the white solid by filtration and wash with water (1×200 mL, 1×130 mL). Dry the white solid in a vacuum oven over solid potassium hydroxide at 50° C. to afford the title compound (222.6 g). ES/MS m/z 217 (M+1).

Example 20

(2R)-2-[8-(2-Chlorophenyl)-2-methyl-6-(4-methylpiperazin-1-yl)purin-9-yl]propan-1-ol; oxalic acid

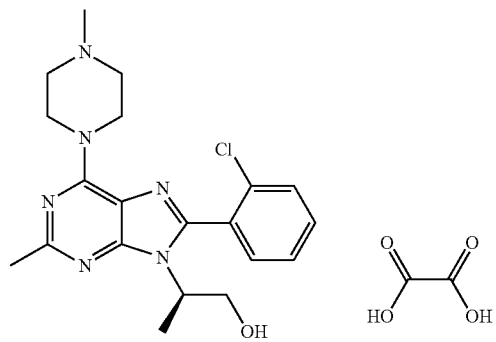 [SMILES: Cc1nc(N2CCN(C)CC2)c2nc(-c3ccccc3Cl)n([C@H](C)CO)c2n1 ; O=C(O)C(=O)O]

Dissolve (2R)-2-[(5-amino-6-chloro-2-methyl-pyrimidin-4-yl)amino]propan-1-ol (228 g, 1.05 mol) and 1-methylpiperizine (210.80 g, 233.9 mL, 2.1) in dimethyl sulfoxide (3.16 L) in a 10 L jacketed reactor open to the air. Add 2-chlorobenzaldehyde (221.88 g, 1.58 mol.) to the flask followed by triethylamine (127.78 g, 176 mL, 1.26 mol) and nitrobenzene (129.55 g, 1.05 mol). Heat the mixture to 140° C. for 3.5 h and then allow to cool. Stir at room temperature for 18 h.

Pour the reaction mixture into water (7.5 L) contained in a 20 L flask while stirring. After 30 min extract the dark brown oil with dichloromethane (1×7.5 L, 1×5 L) and separate the organic layer. Dry the combined organic layers over sodium sulfate, filter, and evaporate to provide an oil. Dissolve the oil in tetrahydrofuran (3.2 L) and treat with a solution of oxalic acid (94.74 g, 1.05 mol, 1 eq) in tetrahydrofuran (2.1 L) with rapid stirring. Warm the reaction mixture to 45° C. for 15 min and then filter the hot mixture under gravity filtration. Wash the filter cake several times with ethyl acetate-tetrahydrofuran (1:1) and finally with ether, while manually agitating the solids. Dry the solids in a vacuum oven to afford the title compound as a light brown solid (329.4 g). $[\alpha]_D$ @ 20° C.=−6, Conc=0.101 g/100 mL (MeOH).

Example 20a (2R)-2-[8-(2-Chlorophenyl)-2-methyl-6-(4-methylpiperazin-1-yl)purin-9-yl]propan-1-ol

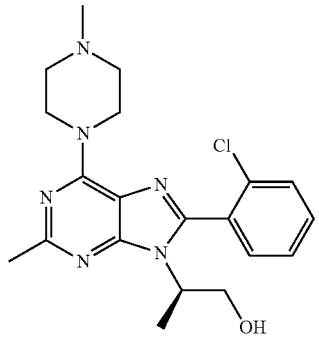 [SMILES: Cc1nc(N2CCN(C)CC2)c2nc(-c3ccccc3Cl)n([C@H](C)CO)c2n1]

Add (2R)-2-[8-(2-chlorophenyl)-2-methyl-6-(4-methylpiperazin-1-yl)purin-9-yl]propan-1-ol oxalate salt (330.3 g, 674.17 mmol) to a rapidly stirred 2 M aqueous sodium hydroxide (1.01 L, 2.02 mol) solution. Stir for 20 min and then extract with dichloromethane (5 L, then 2.5 L), wash with water (2.5 L), and then brine (1.5 L). Add additional freebase material (15.3 g) (generated in pilot reactions, essentially as described above) to the dichloromethane solution. Dry the dichloromethane solution over sodium sulfate, filter, and evaporate to afford a golden crystalline solid. Dry the solid under vacuum to afford the title compound (264.5 g). ES/MS m/z 401.2 (M+1). $[\alpha]^{20}_D$ −4.1 (c 1, MeOH).

Example 20b (2R)-2-[8-(2-Chlorophenyl)-2-methyl-6-(4-methylpiperazin-1-yl)purin-9-yl]propan-1-ol hydrochloride

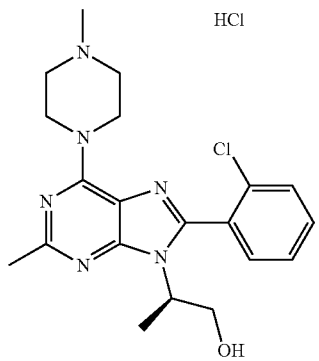 [SMILES: Cc1nc(N2CCN(C)CC2)c2nc(-c3ccccc3Cl)n([C@H](C)CO)c2n1 ; Cl]

Dissolve (2R)-2-[8-(2-chlorophenyl)-2-methyl-6-(4-methylpiperazin-1-yl)purin-9-yl]propan-1-ol (15.29 g, 38.14 mmol) in diethyl ether (114 mL) in a 250 mL round bottom flask, fitted with nitrogen inlet, and treat with 4 N hydrogen chloride in dioxane (9.53 mL, 38.14 mmol). Stir at room temperature for 2.5 h and then collect the solids by vacuum filtration. Wash with diethyl ether (300 mL) and then dry under vacuum to afford the title compound (12.1 g). ES/MS m/z 401.2 (M+1−HCl).

Example 20c (2R)-2-[8-(2-Chlorophenyl)-2-methyl-6-(4-methylpiperazin-1-yl)purin-9-yl]propan-1-ol

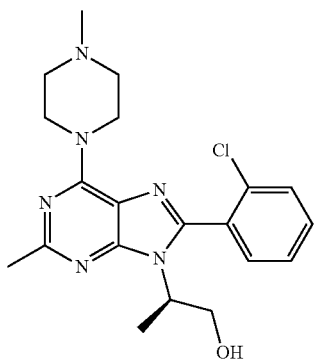 [SMILES: Cc1nc(N2CCN(C)CC2)c2nc(-c3ccccc3Cl)n([C@H](C)CO)c2n1]

In a 2 L flask, treat (2R)-2-[8-(2-chlorophenyl)-2-methyl-6-(4-methylpiperazin-1-yl)purin-9-yl]propan-1-ol (202.1 g, 504.10 mmol) with acetonitrile (1.26 L) and stir at room temperature for 30 min. Collect solids by filtration, wash with acetonitrile (250 mL), air dry and then dry under vacuum at 40° C. to afford the pure title compound (134.1 g). Determine optical purity by chiral SFC to show a single enantiomer. ES/MS m/z 401.2 (M+1). Chiral HPLC conditions: Diacel AD-H, 10% IPA, 0.2% isopropylamine 89.8% supercritical carbon dioxide, UV (220 nm), $T_R$=4.22 min, 100% ee.

Alternate route to (2R)-2-[8-(2-Chlorophenyl)-2-methyl-6-(4-methylpiperazin-1-yl)purin-9-yl]propan-1-ol Preparation 23a 2-chloro-N-[4-chloro-6-[[(1R)-2-hydroxy-1-methylethyl]amino]-2-methyl-pyrimidin-5-yl]benzamide

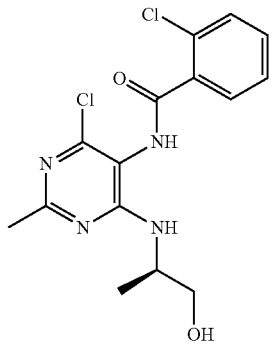 [SMILES: Cc1nc(Cl)c(NC(=O)c2ccccc2Cl)c(N[C@H](C)CO)n1]

Combine 2-chlorobenzoyl chloride (10.44 g, 57.86 mmol), 5-amino-4,6-dichloro-2-methylpyrimidine (10 g, 56.17 mmol) and N-methylpyrrolidone (44 mL) in a 250 mL three-necked round bottom flask equipped with reflux condenser, stirrer bar, and nitrogen inlet/outlet and heat to 80° C. for 5 h. Add water (506 µL) and continue stirring under the heating conditions for 20 min before adding diisopropylethylamine (29.4 mL, 168.52 mmol). Then add (R)-(−)-2-amino-1-propanol (6.23 mL, 79.77 mmol) in one portion followed by a rinse with N-methylpyrrolidone (10 mL). Continue heating at 80° C. for 17 h. Allow the reaction solution to cool to room temperature and then add water (112 mL) dropwise via an addition funnel over 10 min. Continue stirring at room temperature for 35 min and then pour into ethyl acetate (300 mL). Separate the phases and extract the aqueous with ethyl acetate (2×200 mL). Wash the combined organic portions with water (200 mL) and then brine (200 mL), dry over magnesium sulfate, filter, and evaporate to afford an orange oil. Triturate this with tert-butyl methyl ether to afford a white solid, after collection by filtration. Dry the solids on the filter for 0.5 h and then in a vacuum oven at 50° C. to afford the title compound (15.1 g). ES/MS m/z 355.0/357.0 (M+1).

Example 20d (2R)-2-[8-(2-chlorophenyl)-2-methyl-6-(4-methylpiperazin-1-yl)purin-9-yl]propan-1-ol

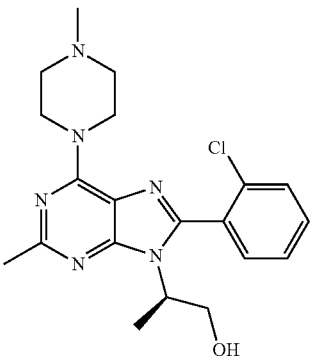 [SMILES: Cc1nc(N2CCN(C)CC2)c2nc(-c3ccccc3Cl)n([C@H](C)CO)c2n1]

Combine 2-chloro-N-[4-chloro-6-[[(1R)-2-hydroxy-1-methyl-ethyl]amino]-2-methyl-pyrimidin-5-yl]benzamide (13.0 g), IPA (11 mL), of N-methylpiperizine (7.1 mL) and diisopropylethylamine (7.0 mL) in a 300 mL Parr autoclave with mechanical stirrer. Seal the reaction vessel and heat to 160° C. for 24 h. Evaporate all volatile materials, dissolve in dichloromethane (100 mL) to give a dark solution. Wash with water (2×50 mL), dry using a hydrophobic frit, and evaporate all the solvent under reduced pressure. Take the resulting solid and dissolve in acetonitrile (85 mL) and stir. After 1.5 h collect the solids by filtration and air dry, before dying under vacuum to provide the title compound (10.73 g). Determine optical purity by chiral SFC to show a single enantiomer. ES/MS m/z 401.2 (M+1). Chiral HPLC conditions: Diacel AD-H, 10% IPA, 0.2% isopropylamine, 89.8% supercritical carbon dioxide, UV (220 nm), $T_R$=4.22 min, 100% ee.

Example 20e (2R)-2-[8-(2-chlorophenyl)-2-methyl-6-(4-methylpiperazin-1-yl)purin-9-yl]propan-1-ol

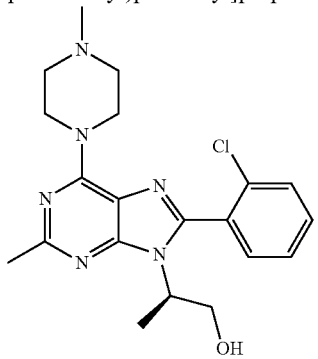

Mix (2R)-2-[8-(2-chlorophenyl)-2-methyl-6-(4-methylpiperazin-1-yl)purin-9-yl]propan-1-ol (800 mg, Example 20a) with acetonitrile (5 mL). Stir the resulting clear dark brown solution at 500 rpm at room temperature, and after a minute of stirring, a white solid begins to precipitate. Stir the sample for 10 min to allow as much material as possible to precipitate out of solution. Isolate the white solid by vacuum filtration and rinse with 1 mL of acetonitrile. Dry the material in a vacuum oven at 85° C. for one hour to recover 505 mg. XRD diffraction peaks using CuKa radiation as source ($\lambda$=1.54060 Å) are set out in the table below.

| Peak | Angle (°2-Theta) +/− 0.2° | Relative Intensity (% of most intense peak) | d value (angstroms) |
|---|---|---|---|
| 1 | 8.26 | 100.00 | 10.69 |
| 2 | 19.68 | 96.50 | 4.51 |
| 3 | 14.81 | 60.60 | 5.98 |
| 4 | 13.20 | 59.20 | 6.70 |
| 5 | 23.92 | 57.10 | 3.72 |
| 6 | 15.97 | 53.30 | 5.55 |
| 7 | 23.08 | 49.60 | 3.85 |
| 8 | 25.70 | 44.40 | 3.46 |
| 9 | 10.93 | 37.90 | 8.09 |
| 10 | 21.02 | 27.90 | 4.22 |

Example 21

{1-[8-(2-Chloro-phenyl)-2-methyl-6-(4-methyl-piperazin-1-yl)-purin-9-yl]-cyclopropyl}methanol hydrochloride

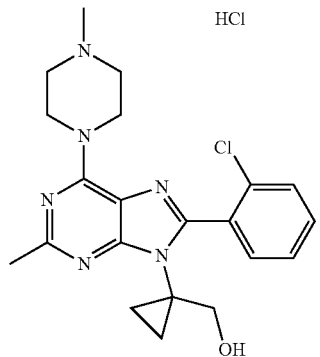 [SMILES: Cc1nc(N2CCN(C)CC2)c2nc(-c3ccccc3Cl)n(C3(CO)CC3)c2n1 ; Cl]

Stir a solution of 1-(5-amino-6-chloro-2-methyl-pyrimidin-4-ylamino)-cyclopropyl]-methanol (1.165 g, 5.09 mmol) and N-methylpiperizine (622.70 μL, 5.60 mmol) in methoxybenzene (15.28 mL) with the flask open to air. Add, in one portion, 2-chlorobenzaldehyde (860.03 μL, 7.64 mmol), followed by nitrobenzene (522.22 μL, 5.09 mmol) and increase the temperature to 140° C. Stir the reaction at 140° C. for 10 h. Transfer the reaction to a rotary evaporator to remove the volatiles. Dilute with 2 N hydrochloric acid (500 mL) and wash with dichloromethane (500 mL). Discard the organic layer and treat the acid fractions with aqueous concentrated sodium hydroxide until pH=14. Extract the product with dichloromethane, dry over $MgSO_4$ and evaporate to afford a brown oil.

Purify the crude material using normal phase SFC (Dintrophenyl column, 20% MeOH (0.2% Diethylmethylamine), 80% CO2). Prepare the HCl salt by dissolving the freebase in water:acetonitrile, 2:1 or another suitable organic solvent, then add with stirring a solution of aqueous or ethereal HCl. Lyophilize to afford the hydrochloride salt of the title compound (390 mg) as a solid. ES/MS m/z 413 (M+1).

Prepare the phenyl piperazinylpurines in the table below by essentially following the procedure as described in Example 21, using the appropriately substituted diamino pyrimidine, 2-chlorobenzaldehyde, and N-methyl or N-ethylpiperazine.

| Ex | Chemical name | Structure | ES/MS m/z |
|---|---|---|---|
| 22 | 1-[8-(2-Chloro-phenyl)-2-methyl-6-(4-methyl-piperazin-1-yl)-purin-9-yl]-2-methyl-propan-2-ol hydrochloride[a] | 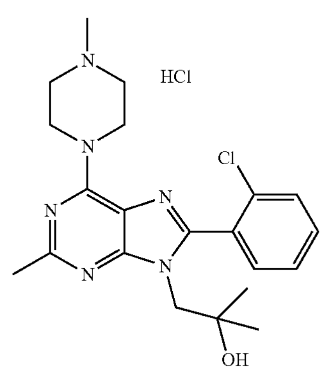 [SMILES: Cc1nc(N2CCN(C)CC2)c2nc(-c3ccccc3Cl)n(CC(C)(C)O)c2n1 ; Cl] | 415 (M + 1) |

| Ex | Chemical name | Structure | ES/MS m/z |
|---|---|---|---|
| 23 | 8-(2-Chloro-phenyl)-6-(4-ethyl-piperazin-1-yl)-9-(2-methoxy-1-methoxymethyl-ethyl)-2-methyl-9H-purine hydrochloride[b] | 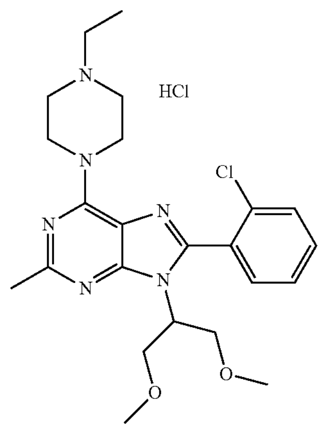 [SMILES: CCN1CCN(c2nc(C)nc3c2nc(-c2ccccc2Cl)n3C(COC)COC)CC1 ; Cl] | 459 (M + 1) |

[a]Purify by preparative reverse phase HPLC: Phenomenex Gemini®, 5 micron C-18 column; Eluent: 10 to 100% acetonitrile in water with 0.1% TFA.
[b]Purify by normal phase silica gel chromatography. Eluent: 0-10% 7M NH$_3$ in MeoH/DCM.

Preparation 24

1-[8-(2-Chlorophenyl)-2-methyl-6-piperazin-1-yl-purin-9-yl]-2-methyl-propan-2-ol

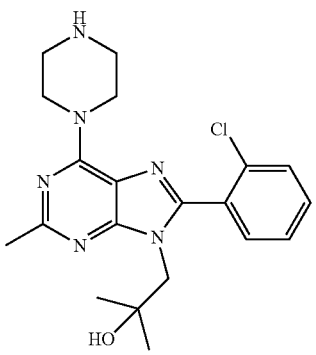 [SMILES: Cc1nc(N2CCNCC2)c2nc(-c3ccccc3Cl)n(CC(C)(C)O)c2n1]

Add trifluoroacetic acid (10 mL) to a solution of tert-butyl 4-[8-(2-chlorophenyl)-9-(2-hydroxy-2-methyl-propyl)-2-methyl-purin-6-yl]piperazine-1-carboxylate (1.9 g, 0.0038 mol) in dichloromethane (10 mL) at 0° C. and stir for 2 h at room temperature. Quench the reaction mixture with saturated sodium bicarbonate solution and extract with dichloromethane. Dry the organic layer over anhydrous sodium sulfate, filter, and concentrate to give the title compound (1.5 g). ES/MS m/z 401 (M+1).

Example 24

Methyl 4-[8-(2-chlorophenyl)-9-(2-hydroxy-2-methyl-propyl)-2-methyl-purin-6-yl]piperazine-1-carboxylate hydrochloride

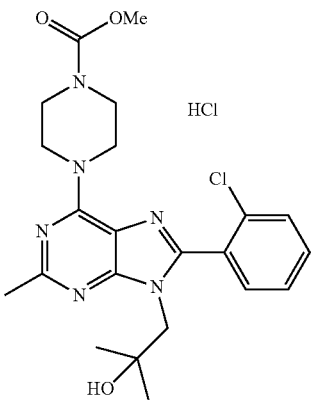 [SMILES: COC(=O)N1CCN(c2nc(C)nc3c2nc(-c2ccccc2Cl)n3CC(C)(C)O)CC1 ; Cl]

Add methyl chloroformate (0.29 g, 0.0031 mol) to a solution of 1-[8-(2-chlorophenyl)-2-methyl-6-piperazin-1-yl-purin-9-yl]-2-methyl-propan-2-ol (0.001 mol, 0.5 g) and pyridine (2.0 mL) in dry dichloromethane (3 mL) at 0° C. and stir for 2 h at room temperature. Quench the reaction mixture with saturated sodium bicarbonate solution and extract with dichloromethane. Dry the organic layer over anhydrous sodium sulfate, filter, and concentrate to give a residue. Purify the residue on a silica gel column using methanol:dichloromethane (3:97) as eluent to give Methyl 4-[8-(2-chlorophenyl)-9-(2-hydroxy-2-methyl-propyl)-2-methyl-purin-6-yl]piperazine-1-carboxylate (0.3 g). ES/MS m/z 459 (M+1).

Add HCl (2.0 M solution in ether) (0.023 g, 0.0006 mol) to a solution of methyl 4-[8-(2-chlorophenyl)-9-(2-hydroxy-2-methyl-propyl)-2-methyl-purin-6-yl]piperazine-1-carboxylate (0.3 g, 0.0006 mol) in ether (4 mL) at 0° C. and stir for 2 h at room temperature. Filter the precipitate, wash with ether,

Example 25

8-(2-Chlorophenyl)-6-(4-ethylpiperazin-1-yl)-9-(methoxymethyl)-2-methyl-purine

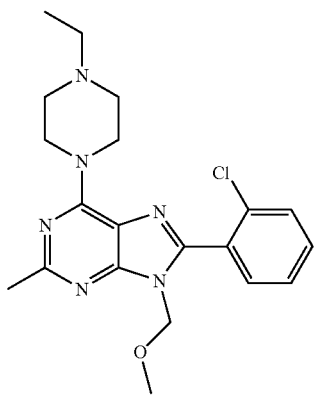 [SMILES: CCN1CCN(c2nc(C)nc3c2nc(-c2ccccc2Cl)n3COC)CC1]

Add sodium hydride (0.031 g, 0.0013 mol) to a solution of 8-(2-chlorophenyl)-6-(4-ethylpiperazin-1-yl)-2-methyl-9H-purine (0.233 g, 0.00065 mol) in dry tetrahydrofuran (20 mL) at 0° C. Stir the reaction mixture for 15 min, then cool to −30° C. and add bromomethyl methyl ether (0.081 g, 0.00065 mol). Warm the reaction mixture to room temperature and stir for one hour. Quench the reaction mixture with water, remove the tetrahydrofuran by evaporation and then extract the reaction mixture with dichloromethane. Dry the organic layer over anhydrous sodium sulfate, filter, and concentrate to give the residue. Purify the residue through preparative reverse phase HPLC (X-Bridge column, 5 mM NH$_4$OAc/acetonitrile) to give the title compound (0.029 g). ES/MS m/z 401 (M+1).

Preparation 25

2-[(5-amino-6-chloro-2-methyl-pyrimidin-4-yl)amino]ethanol

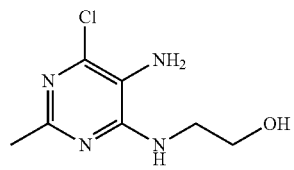

Charge a 1 L auto-clave with 5-amino-4,6-dichloro-2-methylpyrimidine (50.0 g, 0.281 mol), 2-amino ethanol (18.8 g, 0.309 mol), diisopropylethylamine (54.5 g, 0.421 mol), and IPA (500 mL). Heat the mixture to 145-155° C., with stirring for 24 to 30 h. Cool the reaction to 25-30° C. Concentrate the reaction mixture, removing the solvent under vacuum below 50° C. Charge DCM (500 mL) into the mixture and stir at 10-25° C. for 2 h. Filter the mixture and dry the cake in the oven at 45-50° C. to give the product as a pale yellow solid (35.0 g). $^1$H NMR (dmso-d$_6$): δ 6.76 (s, 1H); 4.79 (s, 3H); 3.53-3.37 (m, 4H); 2.09 (s, 3H).

Preparation 26

2-[6-chloro-8-(2-chlorophenyl)-2-methyl-purin-9-yl]ethanol

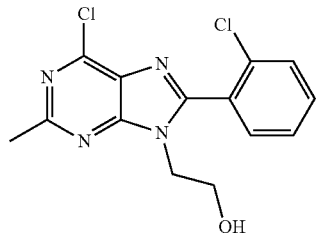 [SMILES: Cc1nc(Cl)c2nc(-c3ccccc3Cl)n(CCO)c2n1]

Charge a 500 mL three-necked round bottom flask with 2-[(5-amino-6-chloro-2-methyl-pyrimidin-4-yl)amino]ethanol (13.0 g, 0.064 mol) and 1,4-dioxane (300 mL). Add 2-chlorobenzaldehyde (13.5 g, 0.096 mol) followed by iron (III) chloride, 5 wt % on silica gel (37.5 g) in one portion. Heat the mixture to 100-105° C. for 48 h. Cool to 20-35° C., filter and rinse the cake with 1,4-dioxane (40 mL). Combine the filtrates and concentrate under vacuum. Dissolve the residue with dichloromethane (260 mL, 20 mL/g) and cool to 0-5° C. Add 2,3-dichloro-5,6-dicyano-1,4-benzoquinone (14.5 g, 0.064 mol) at 0° C., warm up the mixture to 10-25° C., and stir for 2 h. Filter and rinse the cake with ethanol (100 mL) and combine the filtrates. Concentrate down the filtrates under vacuum to give a dark residue. Re-dissolve the residue with dichloromethane (300 mL), wash this solution with 1 N aqueous sodium hydroxide to pH 10-11 followed by water (2×60 mL). Concentrate the organic layer to give crude material. Purify the crude over 400 g silica gel, eluting with dichloromethane/methanol (50:1) to afford a yellow solid (6.5 g). $^1$H NMR (dmso-d$_6$): δ 7.73-7.56 (m, 4H); 4.83 (t, J=6 Hz, 1H); 4.12 (t, J=6 Hz, 2H); 3.61 (q, J=6 Hz, 2H); 2.73 (s, 3H).

Preparation 27

(±)-2-[8-(2-chlorophenyl)-9-(2-hydroxyethyl)-2-methyl-purin-6-yl]-1,3,4,7,8,8a-hexahydropyrrolo[1,2-a]pyrazin-6-one

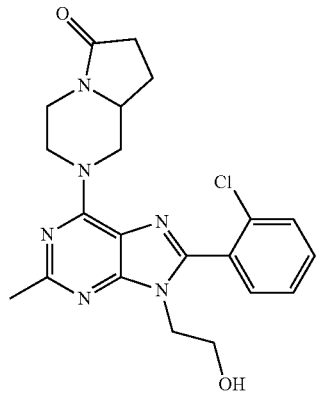 [SMILES: Cc1nc(N2CCN3C(=O)CCC3C2)c2nc(-c3ccccc3Cl)n(CCO)c2n1]

Charge a 500 mL three necked round bottomed flask with 2-[6-chloro-8-(2-chlorophenyl)-2-methyl-purin-9-yl]ethanol (13.3 g, 0.0412 mmol) and ethanol (200 mL), followed by 2,3,4,7,8,8a-hexahydro-1H-pyrrolo[1,2-a]pyrazin-6-one (6.365 g, 0.0453 mol) and triethylamine (14.8 mL, 3.5 eq). Heat the mixture to 80-85° C. for 24 h. Cool the reaction to room temperature and concentrate under vacuum to give a yellow solid as the crude product. Purify the crude material by column chromatography, using 400 g of silica gel and eluting with dichloromethane/methanol (50:1), to give the product as a yellow solid (13.3 g). $^1$H NMR (dmso-d$_6$): δ 7.55-7.41 (m, 4H); 5.72 (bs, 2H); 4.16-3.92 (m, 3H); 3.71 (s, 2H); 3.71-3.68 (m, 1H); 3.02-2.93 (m, 2H); 2.74 (m, 1H); 2.70 (s, 3H); 2.44 (m, 2H); 2.32-2.29 (m, 1H); 1.76-1.69 (m, 1H).

Example 26

2-[8-(2-chlorophenyl)-9-(2-hydroxyethyl)-2-methyl-purin-6-yl]-1,3,4,7,8,8a-hexahydropyaolo[1,2-a]pyrazin-6-one, Isomer 2

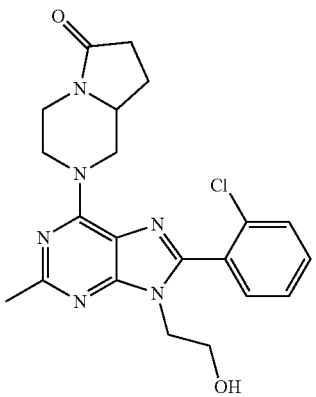 [SMILES: Cc1nc(N2CCN3C(=O)CCC3C2)c2nc(-c3ccccc3Cl)n(CCO)c2n1]

Dissolve (±)-2-[8-(2-chlorophenyl)-9-(2-hydroxyethyl)-2-methyl-purin-6-yl]-1,3,4,7,8,8a-hexahydropyrrolo[1,2-a]pyrazin-6-one (19.0 g) in methanol (400 mL). Separate the enantiomers using supercritical fluid chromatography (AD-H column, 250×30 mm, 5 μm); Mobile phase: A: supercritical CO$_2$; B: MeOH 0.05% diethylamine, A:B=75:25 at 85 mL/min. Detector wavelength is 254 nm. Evaporate the solvents to obtain a yellow solid of Peak 2. Dissolve in dichloromethane (100 mL), wash with water (2×30 mL), decant, and concentrate the organic solution under vacuum below 50° C. to give 7.2 g (99.8% ee) of Isomer 2 as a white solid.

Example 27

2-[8-(2-chlorophenyl)-9-(2-methoxyethyl)-2-methyl-purin-6-yl]-1,3,4,7,8,8a-hexahydropyrrolo[1,2-a]pyrazin-6-one hydrochloride, Isomer 2

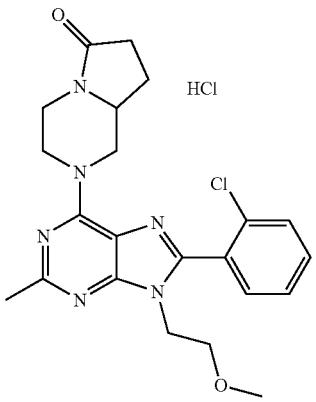 [SMILES: COCCn1c(-c2ccccc2Cl)nc2c(N3CCN4C(=O)CCC4C3)nc(C)nc21 ; Cl]

Charge a 100 mL flask with 2-[8-(2-chlorophenyl)-9-(2-hydroxyethyl)-2-methyl-purin-6-yl]-1,3,4,7,8,8a-hexahydropyrrolo[1,2-a]pyrazin-6-one, Isomer-2 [C09111070-E] (3.3 g, 7.73 mmol) and DMF (35 mL) followed by methyl iodide (1.24 g, 8.50 mmol). Add 60% NaH (0.59 g, 13.9 mmol) in portions at 10-25° C. and stir for 2 h. Pour the mixture into water (100 mL) while stirring and extract the solution with ethyl acetate (3×50 mL). Combine the organic layers, wash with water (2×50 mL), and concentrate under vacuum to give an oil. Purify the crude by silica gel (100 g) column chromatography eluting with dichloromethane/methanol (50:1) to give a yellow solid. Redissolve the solid in ethyl acetate (40 mL) and add a solution of 1 N HCl in ethyl acetate slowly until a solid precipitates. Stir at room temperature for 2 h, filter the cake, and wash with ethyl acetate (10 mL). Dry the cake under vacuum to give 2.8 g of the title compound as an off-white solid (98.0% ee); ES/MS m/z 441.3 (M+1).

CB$_1$ and CB$_2$ In Vitro Functional Assays

Exemplified compounds are tested in agonist mode using a SPA based GTP-γ-$^{35}$S binding assay. All assay components are prepared in assay buffer made up of 20 mM HEPES, 100 mM NaCl, 5 mM MgCl$_2$, (pH 7.4 at room temperature). Semi-log compound dilutions are done in assay buffer containing BSA (final 0.125%). GTP-γ$^{35}$-S binding is measured in a 96 well format using a whole membrane capture technique for the CB$_1$ assay and modifications of an antibody capture technique previously described (DeLapp et al. *J Pharmacol Exp Ther* 289:946-955, 1999) for the CB$_2$ assay. All incubations are done at room temperature.

CB$_1$:

hCB$_1$-CHO membranes, GDP (1 uM final), and saponin (10 ug/mL final) are added to assay buffer and homogenized. Diluted compounds, GTP-γ-$^{35}$S (500 nM final) and membranes are added to the assay plate and incubated for 30 minutes. Then 1 mg/well Wheatgerm Agglutinin SPA bead is added, and the plates are sealed, vortexed, and incubated for an additional hour. Plates are then centrifuged at 700×g for 10 minutes and counted for 1 minute per well using a scintillation counter.

CB$_2$-Sf9:

hCB$_2$-Sf9 membranes and GDP (1 uM final) are added to assay buffer and homogenized. Diluted compounds and membranes are added to the assay plate and pre-incubated for 15 minutes. This is followed by addition of GTP-γ-$^{35}$S (500 nM final) and another 35 minute incubation. Next a mixture containing Nonidet P40 detergent (0.2% final), anti-Gi antibody (final dilution of 1:362), and 1.25 mg anti-rabbit antibody scintillation proximity assay beads are added. The plates are then sealed, vortexed, and incubated for an additional 2 hours before centrifuging and counting as for CB$_1$.

To analyze data, first subtract background from all wells. Determine percent agonist efficacy by normalizing agonist/inverse agonist dose response data to a full agonist (methanandamide) response. Analyze the data using a 4-parameter logistic reduced fit with Activity Base and XLFit3.

All of the exemplified compounds were tested essentially as described above and each was found to have a relative EC50 value for CB$_2$ of ≤100 nM. Example 6 has a relative EC50 value for CB$_2$ of 2.7 nM and for CB$_1$ of >100000 nM. Example 19 has a relative EC50 value for CB$_2$ of 22.4 nM and for CB$_1$ of >100000 nM.

Thus, compounds of the present invention show CB$_2$ in vitro activity. Further, compounds of the present invention show selectivity for CB$_2$ over CB$_1$ and so provide limited potential for centrally mediated side effects.

Displacement of 3H-CP55940 from Human and Rat $CB_2$ Receptors

The methods of Felder et al. (*Mol. Pharmaocol.* 48:443-450, 1995) were utilized with minor modifications. Specifically, membrane homogenates from cells stably or transiently expressing the human or rat $CB_2$ receptor were washed by centrifugation and diluted into a 50 mM Tris HCl (pH 7.4), 5 mM $MgCl_2$, 2.5 mM EDTA, and 0.1% BSA buffer. Specific binding of 3H-CP55940 was defined with 1 µM CP55940. The ability of compounds to displace specific 3H-CP55940 binding was tested over a range of concentrations in the Tris, $MgCl_2$, EDTA, BSA buffer in the presence of 1% dimethyl sulfoxide by incubating at room temperature for 90 minutes in a volume of 300 µl. Unifilter 96-well microplates pretreated with 0.5% polyvinylpyrrolidone, 0.1% polysorbate 20 in water were washed three times with cold Tris buffer. The reaction mixture was then transferred to the filter plate immediately before terminating the incubation by rapid filtration and three 200 µl washes with cold Tris buffer. After the filter plates dried, microscint 20 was added to each well, the plate sealed and counted for determination of disintegrations per minute. The displacement curves were graphed and the resulting Ki values determined utilizing Graphpad Prism.

Example 8 has a human receptor Ki value of 142 nM and a rat receptor Ki value of 37.5 nM. Example 13 has a human receptor Ki value of 65.2 nM and a rat receptor Ki value of 215 nM.

Thus, compounds of the present invention are shown to bind to both human and rat $CB_2$ receptors in vitro.

Monoiodoacetate (MIA) Model

For all studies male Lewis rats of approximately 8 weeks of age at the time of MIA injection are used to measure pain in the MIA model. The rats are housed in groups of 2 or 3 per cage and maintained in a constant temperature and on a 12 hour light/12 hour dark cycle. Animals have free access to food and water at all times except during data collection.

In the standard MIA model the right knees of each rat are injected with 0.3 mg MIA in 50 ul of saline and the left knees with 50 ul of saline. Pain is measured at varying times after MIA injection (not normally before 10 day post MIA injection) using incapacitance testing. This measures the difference in hind paw weight bearing between the MIA and saline injected knees, and each measurement is the average of 3 separate measurements each measured over 1 second.

For studies with $CB_2$ agonists rats are randomized into dose groups (n=5 or 6) and then dosed once with the compound under investigation. Dosing is staggered by 15 minutes for each rat and at a predetermined time post-dose (usually 2 hours), pain measured using incapacitance testing. Studies are routinely run with 4 groups, vehicle (1% carboxy methyl cellulose in water plus 0.25% polysorbate 80) and 3 compound groups which can be either single compounds at a single dose or the same compound at 3 doses. Results are reported as the difference in weight bearing between saline and MIA injected knees and statistical comparisons are made between vehicle treated and compound treated animals to assess the effect of compounds on knee pain in the model.

Example 19 was tested essentially as described above and found to reduce pain versus vehicle at doses of 0.3 and 1 mg/kg. Example 18 was tested essentially as described above and found to reduce pain versus vehicle at a dose of 0.3 mg/kg.

Thus, compounds of the present invention are shown to be useful in the treatment of pain, in particular joint pain.

Chemotherapy-Induced Pain Assay

Male Harlan Sprague Dawley rats 150-200 grams are acclimated to the vivarium for 7 days. The animals are maintained in a constant temperature and on a 12 hour light/12 hour dark cycle, and housed in groups of 3-4 with water and food ad libitum. Twice daily dosing of compound at 10 mg/kg (oral), morphine at 5 mg/kg, and vehicle commences on Day 1 of the study, and continues through the duration of the study (Day 18). Paclitaxel at 1 mg/kg (intraperitoneal) is administered on Days 2, 4, 6, and 8, for a cumulative dose of 4 mg/kg in order to induce chemotherapy-induced peripheral neuropathy.

Rats are placed in individual plexiglass chambers with a wire mesh platform bottom to allow access to the hindpaw. After an acclimation period of 15 minutes to 1 hour, the mid-plantar hind paws are assessed within the sciatic nerve distribution. A series of 8 von Frey hairs with logarithmically incremental stiffness (0.41, 0.70, 1.20, 2.00, 3.63, 5.50, 8.50, and 15.10 g) are applied to the hind paws. The von Frey hairs are presented perpendicular to the plantar surface with sufficient force to cause slight bending. Stimuli are presented at intervals of several seconds. A positive response is noted if the paw is sharply withdrawn or if flinching immediately upon removal of the hair is observed. On study days, behavioral endpoints are evaluated 1 hour post-dose. Score patterns are evaluated using the Dixon up-down method, and translated to a response threshold (1980, Ann Rev Pharmacol Toxicol 20:441-462). The maximum applied force is 15.10 grams. The initial behavior assessment occurs on Day 10 of the study, and subsequent measures are made on Study Days 12, 15, and 18.

Results are expressed as mean values with standard errors of the mean (mean±SE) for an n of 12 per group. All statistical evaluations are conducted utilizing a one-way ANOVA followed by comparison to the control group by Dunnett's Method. Statistical significance is assumed when $p<0.05$. Statistical analyses are performed using JMP statistical analysis software (SAS Research Institute, version 6.0.2).

|  | Vehicle (mean ± SE) | Example 19 10 mg/kg (mean ± SE) | Morphine 5 mg/kg (mean ± SE) |
| --- | --- | --- | --- |
| Day 10 | 7.83 ± 1.35 | 11.25 ± 1.31 | 8.16 ± 1.22 |
| Day 12 | 7.12 ± 1.27 | 7.38 ± 0.95 | 3.67 ± 0.30* |
| Day 15 | 4.86 ± 0.95 | 7.90 ± 1.04* | 3.84 ± 0.45 |
| Day 18 | 3.27 ± 0.34 | 6.02 ± 0.72* | 3.46 ± 0.42 |

*Indicates statistical significance

Mean paw withdrawal latencies with standard errors are shown for Example 19, morphine, and vehicle in the above table. Compared to both vehicle and morphine-treated animals, Example 19-treated animals developed less allodynia over the duration of the study. Thus, Example 19 of the present invention is shown to be useful in the prevention of pain, in particular chemotherapy-induced pain such as chemotherapy-induced peripheral neuropathy.

Dose-Ranging Toxicity Study in Beagle Dogs

One male and one female beagle dog are used to evaluate the acute toxicity after a single oral gavage dose of $CB_2$ agonist. The dogs are housed individually and maintained in a constant temperature and on a 12 hour light/12 hour dark cycle. $CB_2$ agonist is prepared in vehicle (1% hydroxyethylcellulose, 0.25% polysorbate 80, and 0.05% Dow Corning® Antifoam 1510-US in purified water) and administered by oral gavage at a dose volume of 2 mL/kg. Dogs are observed for mortality and clinical observations (before dosing, 2 hours postdose, in the afternoon and daily thereafter). Food consumption is assessed by daily visual assessment of food remaining. Blood is collected before dosing and 48 hours after dosing to evaluate effects on haematology and clinical chemistry parameters. Blood is collected at 0.5, 1, 2, 4, 8, and 24 hours postdose to evaluate toxicokinetic plasma drug concentrations.

Example 19 was tested essentially as described above at a single oral dose of 30 mg/kg. Post-dose clinical observations were limited to vomiting and dilated pupils. Vomiting was noted only in the female dog at 19 minutes, 39 minutes and 2 hours post-dose. Dilated pupils were noted in the male and female dogs from 2 to 4 hours post-dose. Decreased faeces and minimal decreased food consumption was also noted in the female dog. Effects on haematology were limited to a slight decrease in reticulocyte count in the female dog (39% change relative to pre-dose). The mean Area-Under the Curve from 0-24 hours ($AUC_{0-24hr}$) at 30 mg/kg was 44451 ng·hr/mL. The mean maximum concentration ($C_{max}$) at 30 mg/kg was 7537 ng/mL.

Thus, certain compounds of the present invention are shown to have limited toxicity in dogs at 30 mg/kg and as a result the potential for an acceptable side effect profile in humans.

We claim:

1. A compound of the formula:

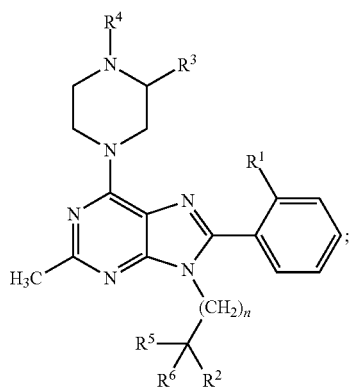

(I)

wherein;
$R^1$ is $C_1$ or $CH_3$;
$R^2$ is OH, $OCH_3$, $CH_2OH$ or $CH_2OCH_3$;
$R^3$ is H or combines with $R^4$ to form a fused pyrrolidin-2-one;
$R^4$ is $C_1$-$C_2$ alkyl, $C_1$-$C_2$ fluoroalkyl, $C(O)CH_3$ or $CO_2CH_3$;
$R^5$ is H, $CH_3$ or $CH_2OCH_3$;
$R^6$ is H, $CH_3$ or combines with $R^5$ to form a cyclopropane ring; and
n is 0 or 1;
or a pharmaceutically acceptable salt thereof.

2. A compound according to claim 1, or a pharmaceutically acceptable salt thereof, wherein $R^1$ is Cl.

3. A compound according to claim 1, or a pharmaceutically acceptable salt thereof, wherein $R^2$ is OH or $CH_2OH$.

4. A compound according to claim 1, or a pharmaceutically acceptable salt thereof, wherein $R^2$ is $CH_2OH$.

5. A compound according to claim 1, or a pharmaceutically acceptable salt thereof, wherein $R^3$ is H and $R^4$ is methyl, ethyl, 2-fluoroethyl or $C(O)CH_3$.

6. A compound according to claim 1, or a pharmaceutically acceptable salt thereof, wherein $R^3$ is H and $R^4$ is methyl.

7. A compound according to claim 1, or a pharmaceutically acceptable salt thereof, wherein $R^5$ and $R^6$ are independently selected from H and $CH_3$.

8. A compound according to claim 1, or a pharmaceutically acceptable salt thereof, wherein $R^5$ is H and $R^6$ is $CH_3$.

9. A compound according to claim 1, or a pharmaceutically acceptable salt thereof, wherein n is 0.

10. A compound according to claim 1, or a pharmaceutically acceptable salt thereof, wherein $R^1$ is Cl; $R^2$ is OH or $CH_2OH$; and $R^4$ is methyl, ethyl, 2-fluoroethyl or $C(O)CH_3$.

11. A compound according to claim 1, or a pharmaceutically acceptable salt thereof, wherein $R^1$ is Cl; $R^2$ is $CH_2OH$; $R^4$ is methyl, ethyl, 2-fluoroethyl or $C(O)CH_3$; $R^5$ is H and $R^6$ is $CH_3$.

12. A compound according to claim 1 being 2-[8-(2-chloro-phenyl)-2-methyl-6-(4-methyl-piperazin-1-yl)-purin-9-yl]-propan-1-ol, or a pharmaceutically acceptable salt thereof.

13. A compound according to claim 1 being (2R)-2-[8-(2-chlorophenyl)-2-methyl-6-(4-methylpiperazin-1-yl)purin-9-yl]propan-1-ol, or a pharmaceutically acceptable salt thereof.

14. A pharmaceutical composition comprising a compound according to claim 1, or a pharmaceutically acceptable salt thereof, and a pharmaceutically acceptable diluent or carrier.

15. A method for the treatment of pain, which comprises administering an effective amount of a compound according to claim 1, or a pharmaceutically acceptable salt thereof, to a mammal in need thereof.

16. A method according to claim 15 for the treatment of osteoarthritic pain.

17. A method according to claim 15 for the treatment of chemotherapy induced pain.

* * * * *

UNITED STATES PATENT AND TRADEMARK OFFICE
CERTIFICATE OF CORRECTION

| | | |
|---|---|---|
| PATENT NO. | : 8,759,360 B2 | Page 1 of 1 |
| APPLICATION NO. | : 13/072843 | |
| DATED | : June 24, 2014 | |
| INVENTOR(S) | : Adam Jan Sanderson et al. | |

It is certified that error appears in the above-identified patent and that said Letters Patent is hereby corrected as shown below:

In the Claims

Column 45, Line 43, In Claim 1, delete "C1" and insert -- Cl --, therefor.

Column 46, Line 7, In Claim 3, before "claim 1" insert -- to --.

Signed and Sealed this
Second Day of December, 2014

Michelle K. Lee
*Deputy Director of the United States Patent and Trademark Office*